United States Patent [19]

Koppel et al.

[11] 4,144,232

[45] Mar. 13, 1979

[54] SUBSTITUTED AZETIDIN-2-ONE ANTIBIOTICS

[75] Inventors: Gary A. Koppel; Robin D. G. Cooper, both of Indianapolis, Ind.

[73] Assignee: Eli Lilly and Company, Indianapolis, Ind.

[21] Appl. No.: 855,841

[22] Filed: Nov. 30, 1977

Related U.S. Application Data

[63] Continuation-in-part of Ser. No. 753,980, Dec. 23, 1976, abandoned.

[51] Int. Cl.² ............... C07D 205/08; A61K 31/395; C07D 277/60
[52] U.S. Cl. ................... 260/239 A; 546/275; 260/306.6 R; 260/306.8 D; 260/307 R; 260/307 H; 260/307 D; 260/308 D; 260/306.8 A; 260/337.2 R; 260/347.4; 260/306.7 C; 542/454; 424/244; 548/316
[58] Field of Search .......... 260/239 A, 307 H, 307 G, 260/307 R, 306.8 D, 306.8 R, 306.8 A, 332.2 R, 347.4, 295 L, 308 D; 548/316; 542/454

[56] References Cited

U.S. PATENT DOCUMENTS

| | | | |
|---|---|---|---|
| 3,487,071 | 12/1969 | Sheehan | 260/239 A |
| 3,923,977 | 12/1975 | Aoki et al. | 260/239 A |

OTHER PUBLICATIONS

Kamiya et al., Chem. Abs., 85, 21078, (1976).

*Primary Examiner*—Mark L. Berch
*Attorney, Agent, or Firm*—William B. Scanlon; Arthur R. Whale

[57] ABSTRACT

Monocyclic β-lactam antibiotics of the formula

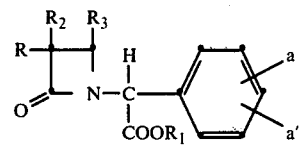

wherein R is amino or acylamino, e.g., phenylacetylamino, phenylglycylamino and 2-[4-(3-amino-3-carboxypropoxy)phenyl]-2-hydroximinoacetylamino; $R_1$ is H or ester forming group; $R_2$ is H, $-OCH_3$, $-SCH_3$, or $-CH_3$; and $R_3$ is H or acetoxy; are useful antibacterials for controlling β-lactamase producing gram-negative bacteria and other pathogens. Intermediates useful in the preparation of the antibiotics and a novel process for preparing 4α-acetoxy substituted azetidin-2-ones are provided.

32 Claims, No Drawings

SUBSTITUTED AZETIDIN-2-ONE ANTIBIOTICS

CROSS-REFERENCE TO RELATED APPLICATION

This application is a continuation-in-part of copending application Ser. No. 753,980 filed Dec. 23, 1976 now abandoned.

BACKGROUND OF THE INVENTION

This invention relates to β-lactam antibiotics. In particular, it relates to monocyclic β-lactam antibiotics which are 3β-acylaminoazetidin-2-ones.

The penicillins and cephalosporins are well known β-lactam antibiotics which are bicyclic compounds containing a fused ring system. The penicillins have the 4-membered β-lactam ring fused to a thiazolidine ring while in the cephalosporins, the β-lactam ring is fused to a dihydrothiazine ring. Monocyclic β-lactam antibacterial compounds are less well known. The monocyclic β-lactam antibiotic, nocardicin, has been recently discovered and is described in Belgium Pat. No. 830,934 and by H. Aoki, et al., 15th Interscience Conference on Antimicrobial Agents and Chemotherapy, Abst. No. 97, Sept. 1975.

Nocardicin has the following structural formula.

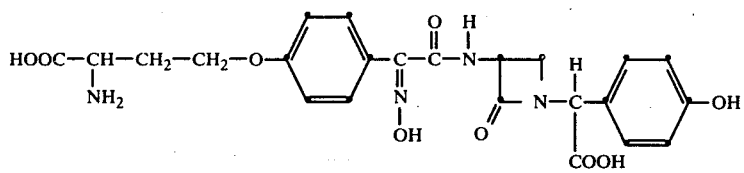

In view of the importance of β-lactam antibiotics in the treatment of infectious diseases, considerable effort is directed by microbiologists and chemists to the discovery and development of other β-lactam antibiotics which possess activity against a broader spectrum of microorganisms or which are more effective than the currently available antibiotics.

SUMMARY

This invention provides 3β-acylaminoazetidin-2-one compounds represented by the formula

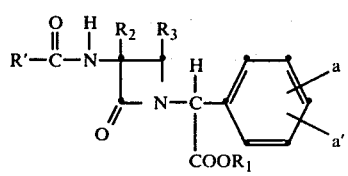

wherein R' is the residue of a carboxylic acid, e.g., lower alkyl, phenyl, benzyl, phenoxymethyl, phenylthiomethyl, α-substituted benzyl wherein the α-substituent is e.g., hydroxy, amino, or carboxy; a heterocyclic group, e.g., thienyl, furyl, isothiazole, isoxazole, or tetrazole; $R_1$ is hydrogen or an ester forming group; $R_2$ is hydrogen, methoxy, methylthio, or methyl; $R_3$ is hydrogen or acetoxy; and a and a' represent optional substituents, e.g., hydroxy, lower alkoxy, lower alkyl, halogen, amino, or aminomethyl; which are useful antimicrobial agents effective in controlling β-lactamase producing bacteria. The azetidinones are prepared with the 3β-aminoazetidin-2-ones represented by the formula

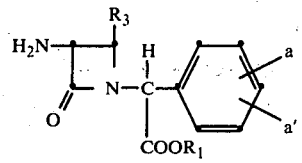

wherein $R_3$ is hydrogen or acetoxy via methylation or methylthiolation of a 3β-benzalimino or substituted 3β-benzalimino derivative, prepared with the above 3β-amino nucleus and a benzaldehyde, followed by hydrolysis of the imine to the methyl or methylthio substituted 3β-amino nucleus and acylation of the nucleus with an active derivative of the R'-COOH carboxylic acid and de-esterification of the $R_1$ ester group. Azetidin-2-ones wherein $R_2$ is methoxy are prepared via methoxylation of a 3β-acylamino azetidin-2-one wherein $R_3$ is hydrogen or acetoxy with methyl lithium in methyl alcohol and t-butyl hypochlorite or other positive organic chlorine compound.

The 3β-amino-4-acetoxyazetidin-2-ones ($R_3$ is acetoxy) are prepared in a novel process via mercuric acetate-acetic acid ring opening of a substituted bicyclic thiazolidine azetidin-2-one.

The substituents $R_2$ and $R_3$ in the 3- and 4-positions have the α-configuration and the preferred azetidin-2-ones are the 4α-acetoxy substituted compounds wherein $R_2$ is hydrogen and $R_3$ is α-acetoxy, in particular, the 4α-acetoxy derivative of the antibiotic nocardicin.

DETAILED DESCRIPTION

The azetidin-2-one compounds of this invention are represented by the following structural formula 1

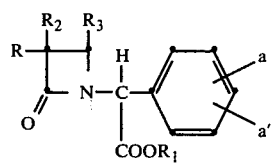

wherein a and a' independently are hydrogen, halogen, hydroxy, benzyloxy, tetrahydropyran-2-yloxy, $C_1$-$C_4$ alkyl, $C_1$-$C_4$ alkoxy, amino or aminomethyl; R is amino or an acylamino group of the formula

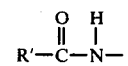

wherein R' is $C_1$-$C_4$ alkyl, cyanomethyl, bromomethyl, chloromethyl, phenyl, or a group of the formula

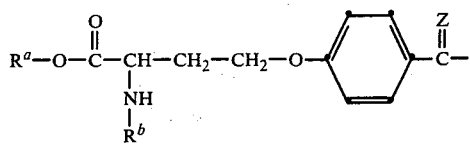

wherein $R^a$ is hydrogen, benzyl, diphenylmethyl or 4-methoxybenzyl;

$R^b$ is hydrogen or an amino-protecting group of the formula

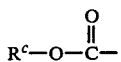

wherein $R^c$ is t-butyl, 2,2,2-trichloroethyl, benzyl, 4-nitrobenzyl, cyclopentyl, or cyclohexyl; Z is =O or =N—OZ', wherein Z' is hydrogen, acetyl, chloroacetyl, triphenylmethyl or p-methoxybenzyl; or R' is a group of the formula

wherein R'' is a phenyl group of the formula

wherein b and b' independently are hydrogen, halogen, hydroxy, $C_1$–$C_4$ alkyl, $C_1$–$C_4$ alkoxy, amino or aminomethyl; or R'' is thienyl, furyl, thiazolyl, oxazolyl, isothiazolyl, tetrazolyl, or an isoxazolyl group of the formula

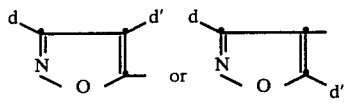

wherein d is hydrogen, methyl, or a group of the formula

wherein b and b' have the same meanings defined above, and d' is hydrogen, methyl, or chloro; or R' is a phenoxymethyl group of the formula

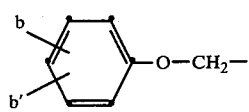

wherein b and b' have the same meanings as defined above; or R' is a group of the formula

wherein R''' is a group of the formula

4-pyridyl, thiazolyl, thiadiazolyl, or oxadiazolyl; or R' is a group of the formula

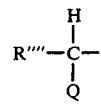

wherein R'''' is a phenyl group of the formula

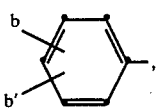

thienyl or furyl, and Q is amino, hydroxy, carboxy, —$SO_3H$, or —NH—$SO_3H$; or R' is a group of the formula

wherein R'''' has the same meanings as defined above and Z'' is hydrogen, acetyl or methyl; or R' is a group of the formula

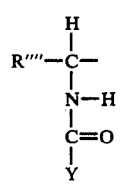

wherein Y is a dimethylureido group of the formula

the imidazolidin-2-one group

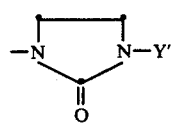

wherein Y' is hydrogen, $C_1$–$C_4$ alkyl, $C_2$–$C_4$ alkanoyl or methanesulfonyl; or an N-methylacyl group of the formula

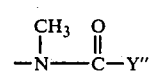

wherein Y'' is $C_1$–$C_4$ alkyl, or a group of the formula

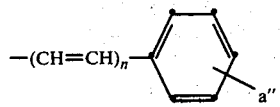

wherein n = 0 or 1 and a'' is hydrogen, nitro, or chloro;

R₁ is hydrogen or a carboxylic acid protecting group;

R₂ is hydrogen, methyl, methylthio, or methoxy;

R₃ is hydrogen or acetoxy, provided that one of R₂ and R₃ is other than hydrogen; and when R₁ is hydrogen the pharmaceutically acceptable non-toxic salts thereof.

The phenyl group represented in the above definition by the formula

represents phenyl, 4-hydroxyphenyl, 4-(tetrahydropyran-2-yloxy)phenyl, 4-benzyloxyphenyl, 3-hydroxyphenyl, 3,4-dihydroxyphenyl, 4-chlorophenyl, 3,4-dichlorophenyl, 2,6-dichlorophenyl, 3-bromophenyl, 3-chloro-4-hydroxyphenyl, 3-chloro-4-methylphenyl, 4-t-butylphenyl, 3,4-dimethylphenyl, 2,4-dimethylphenyl, 4-ethylphenyl, 3-methyl-4-hydroxyphenyl, 4-aminophenyl, 3-aminophenyl, 3-amino-4-methylphenyl, 2-aminomethylphenyl, 4-aminomethylphenyl, 4-methoxyphenyl, 2,6-dimethoxyphenyl, 3-ethoxy-4-hydroxyphenyl, 4-isopropoxyphenyl, 4-chloro-2-aminomethylphenyl, 3-bromo-4-methoxyphenyl, 3-methyl-4-aminophenyl, and like substituted phenyl groups.

The phenyl group represented in the above formula by

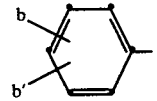

represents phenyl, 4-chlorophenyl, 3,4-dichlorophenyl, 3-bromophenyl, 3-chloro-4-hydroxyphenyl, 4-hydroxyphenyl, 3-hydroxyphenyl, 3,4-dihydroxyphenyl, 4-methylphenyl, 4-t-butylphenyl, 4-ethylphenyl, 4-methoxyphenyl, 3-ethoxy-4-hydroxyphenyl, 4-aminophenyl, 4-aminomethylphenyl, 3-methyl-4-aminophenyl, 2,6-dimethoxyphenyl, 3-bromo-4-methoxyphenyl, and like substituted phenyl groups.

Illustrative of the amino-protecting groups defined in the above formula (1) by the formula

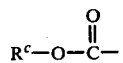

are t-butyloxycarbonyl, 2,2,2-trichloroethoxycarbonyl, benzyloxycarbonyl, p-nitrobenzyloxycarbonyl, cyclopentyloxycarbonyl and cyclohexyloxycarbonyl.

As used herein the term thienyl refers to both 2-thienyl and 3-thienyl; thiazolyl refers to 2-thiazolyl and 5-thiazolyl; tetrazolyl refers to 1- and 2-tetrazolyl; thiadiazolyl refers to 1,3,4- 1,2,5- and 1,2,4-thiadiazol-5-yl; and oxadiazolyl refers to 1,3,4-oxadiazolyl.

Examples of isoxazolyl groups represented in the above formula (1) by

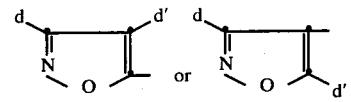

are 3-methylisoxazol-5-yl, 3,4-dimethylisoxazol-5-yl, 4-chloroisoxazol-5-yl, 3-phenyl-4-chloroisoxazol-5-yl, 3-(4-chlorophenyl)isoxazol-5-yl, 3-(2-chlorophenyl)isoxazol-5-yl, 3-(2-chlorophenyl)-4-methylisoxazol-5-yl, 3-(2,6-dichlorophenyl)isoxazol-5-yl, 3-(2,6-dichlorophenyl)-4-methylisoxazol-5-yl, isoxazole-5-yl, 3-(2,4-dimethylphenyl)-4-methylisoxazol-5-yl, 3-(2,6-dimethylphenyl)-4-chloroisoxazol-5-yl, 3(4-methoxyphenyl)isoxazol-5-yl, 3-(2,6-dimethoxyphenyl)-4-chloroisoxazol-5-yl, 3-(3-chloro-4-hydroxyphenyl)-4-methylisoxazol-5-yl, 3-methyl-5-chloroisoxazol-4-yl, 3,5-dimethylisoxazol-4-yl, 3-phenylisoxazol-4-yl, 3-(4-chlorophenyl)-5-methylisoxazol-4-yl, 3-(2-chlorophenyl)-5-chloroisoxazol-4-yl, 3-(2,6-dimethoxyphenyl)-5-methylisoxazol-4-yl and like isoxazoles.

The compounds of the formula (1) can be characterized as monocyclic β-lactam antibiotics or as azetidin-2-ones which are substituted in the 1-position with an α-carboxybenzyl or α-carboxy-substituted benzyl group and in the 3-position by a β-amino or β-acylamino group and which are also substituted in the 3- or 4-, or 3- and 4-positions with one of the groups as defined above in the formula (1).

The compounds of this invention are prepared with the 3β-amino-azetidin-2-one esters represented by the following formulas 2 and 3.

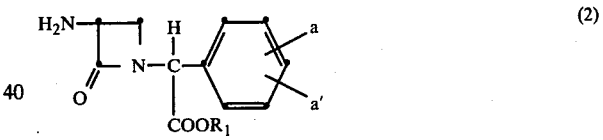

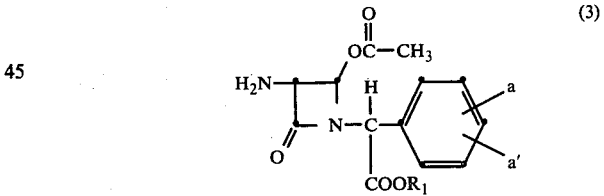

In the above formulas a, a', and R₁ have the same meanings as defined above with respect to formula (1). The esterified 1-(α-carboxybenzyl or substituted-benzyl)-3β-aminoazetidin-2-one (2) is prepared as described hereinafter while the esterified 1-(α-carboxybenzyl or substituted-benzyl)-3β-amino-4α-acetoxyazetidin-2-one (3) is prepared by a novel process which is a further aspect of this invention likewise described hereinafter.

The compounds of the formula (1) wherein R₂ is methyl or methylthio and R₃ is hydrogen or acetoxy are prepared with the 3-amino nucleus esters (2) or (3) as follows. First, the 3β-amino nucleus ester (2) or (3) is reacted in an inert dry solvent with an aromatic aldehyde, for example, benzaldehyde or a substituted benzaldehyde such as 3,4-dichlorobenzaldehyde, 4-bromobenzaldehyde or, preferably, 4-nitrobenzaldehyde, to form the 3β-benzalimino derivative (Schiff's base) as illustrated below wherein nucleus (3) is employed.

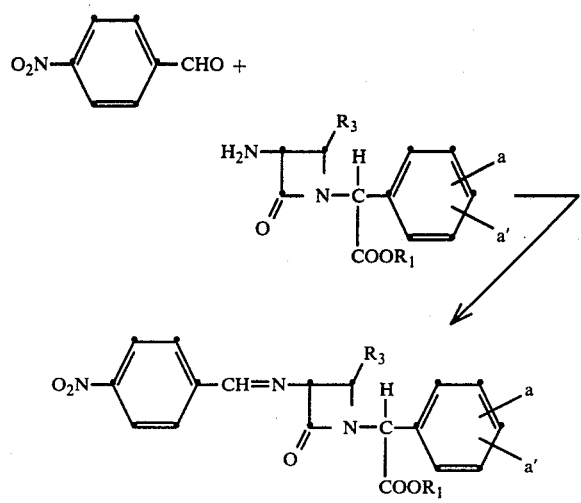

wherein R₃ is H or acetoxy.

The reaction can be carried out in absolute ethyl alcohol at a temperature of 20°–45° C. Other solvents such as methylene chloride and trichloroethane can also be used.

The benzalimino ester is then reacted in an inert anhydrous solvent at a temperature between about −80° and about 0° C. with a strong base such as sodium hydride or an organo lithium base, for example, lithium diisopropyl amide, to generate in situ the Schiff's base in anionic form. The anionic form is then alkylated in the cold with methyl iodide to form the 3-methyl benzalimino ester represented by the formula

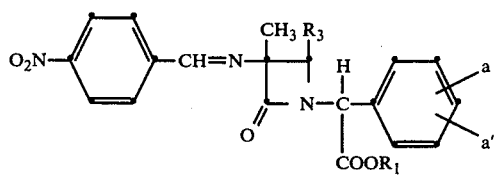

Alternatively, the anionic form of the Schiff's base is reacted in the cold with methoxycarbonyl methyl disulfide to provide the 3-methylthio derivative represented by the formula

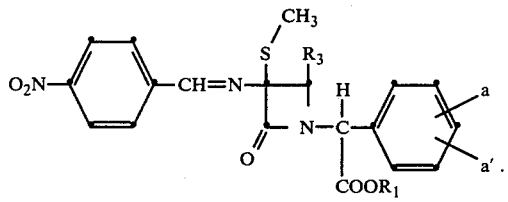

The formation of the anion of the Schiff's base and its methylation and methylthiolation can be carried out in anhydrous dimethylformamide or tetrahydrofuran. When sodium hydride is used as the strong base, the reaction is carried out at about −10° C. to about 0° C. For example, a sodium hydride dispersion containing about 1.1 equivalents of sodium hydride in DMF is cooled to about −5° C. and methyl iodide is added to the dispersion with stirring. With stirring a cold solution of the benzalimine in DMF is added. After the reaction is complete, the mixture is neutralized and the product is extracted with a suitable water-immiscible organic solvent such as ethyl acetate.

The 3-methyl or 3-methylthio-3-benzaliminoazetidin-2-ones are converted to the 3β-amino which is then acylated with the desired carboxylic acid or an active derivative thereof to provide a compound of the formula 1 wherein R₁ is an ester forming group.

The benzalimino ester is converted to the 3-amino nucleus ester when reacted with a suitable aldehyde (carbonyl) reagent such as sodium bisulfite, Girard's reagent T (carboxymethyltrimethylammonium chloride), aminooxyacetic acid hemi hydrochloride or dimedone. The reaction is carried out at a temperature between about 20° C. and about 50° C. in an inert solvent such as tetrahydrofuran, dioxane, water or mixtures of these solvents with the lower alcohols.

The 3β-amino-3-methyl or 3-methylthioazetidin-2-one esters are conveniently isolated from the reaction mixture in the salt form. For example, the p-toluenesulfonic acid salt or α-naphthalenesulfonic acid salts are convenient salt forms for recovering and isolating the nucleus compounds.

In a example of the preparation of a 3β-amino-3-methylazetidin-2-one ester, 1-[α-(benzyloxycarbonyl)-benzyl]-3β-amino-4α-acetoxyazetidin-2-one is reacted in absolute ethyl alcohol with p-nitrobenzaldehyde and the imine, 1-[α-(benzyloxycarbonyl)benzyl]-3β-(p-nitrobenzideneamino)-4α-acetoxyazetidin-2-one, is dissolved in DMF (dried over molecular sieve) and the solution added to a dispersion of sodium hydride in DMF maintained at a temperature of −5° C. Methyl iodide is added to the reaction mixture with agitation and after the reaction is complete, the mixture is neutralized in the cold with dilute aqueous acid and the product extracted with ethyl acetate. The product, 1-[α-(benzyloxycarbonyl)benzyl]-3β-(p-nitrobenzylideneamino)-3-methyl-4α-acetoxyazetidin-2-one, is reacted with aminooxyacetic acid hemi hydrochloride to provide 1-[α-(benzyloxycarbonyl)benzyl]-3β-amino-3-methyl-4α-acetoxyazetidin-2-one represented by the formula

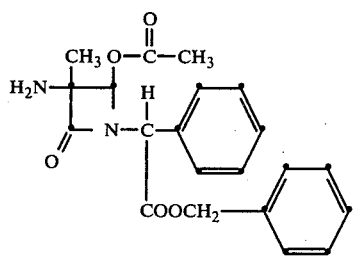

In an example of the preparation of a 3-methylthio nucleus ester, 1-[α-(benzyloxycarbonyl)-4-benzyloxybenzyl]-3β-aminoazetidin-2-one is condensed with p-nitrobenzaldehyde and the 3β-(p-nitrobenzylideneamino)azetidin-2-one ester is reacted in DMF at 5° C. with sodium hydride and methoxycarbonyl methyl disulfide

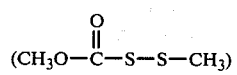

to provide the 3-methylthio substituted azetidin-2-one ester. Hydrolysis of the imine group with aqueous sodium bisulfite provides 1-[α-(benzyloxycarbonyl)-4-benzyloxybenzyl]-3β-amino-3-methylthioazetidin-2-one represented by the formula

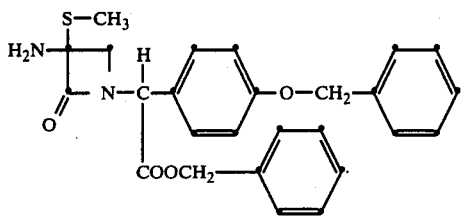

The preparation of the compounds of the invention represented by the formula (1) wherein $R_2$ is methoxy is carried out with an N-acyl derivative of the formula (1) wherein $R_2$ is hydrogen. For example, an N-acyl compound of the formula (1) wherein R is an acylamino group

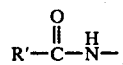

is reacted at a temperature between about −90° C. and about −15° C. in an anhydrous inert solvent with lithium methylate and an excess of methyl alcohol followed by treatment with a positive chlorine containing compound such as t-butylhypochlorite. When the starting N-acylazetidin-2-one ester of the formula (1) contains in the acyl portion a free hydroxy, amino, or acidic function, these functions are preferably protected or blocked during the methoxylation.

In the methoxylation process the lithium methylate is generated in situ with a lithium alkyl such as methyl lithium and methyl alcohol.

Tetrahydrofuran is a suitable solvent in the methoxylation reaction.

In an example of the methoxylation, tetrahydrofuran is cooled in an ice bath and methyl lithium and methyl alcohol are added. The solution is stirred under nitrogen for a few minutes and is then cooled to a temperature of about −80° C. in an acetone-dry ice bath. A solution of 1-[α-(benzyloxycarbonyl)-4-benzyloxybenzyl]-3-phenoxyacetamidoazetidin-2-one in tetrahydrofuran is added with stirring. To the cold mixture is added an excess of t-butyl hypochlorite and the reaction is stirred until complete. The reaction is quenched with glacial acetic acid and the acidified mixture is evaporated to a reaction product mixture and the product 1-[α-(benzyloxycarbonyl)-4-benzyloxybenzyl]-3-phenoxyacetamido-3-methoxyazetidin-2-one represented by the following formula is extracted from the residue with methylene chloride.

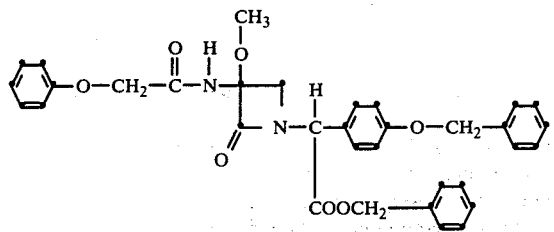

The 3-methyl and 3-methylthio-3-aminoazetidin-2-one esters (formula I, $R=NH_2$, $R_2=CH_3$— or $CH_3$—S—) prepared as described above, are acylated with the desired carboxylic acid $R'COOH$ or an active derivative thereof,

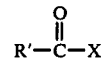

to provide a compound of the formula (1) wherein R is an acylamino group

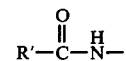

and $R_1$ is a carboxylic acid protecting group.

The acylation can be carried out according to the known N-acylation methods employed in the penicillin and cephalosporin arts for the acylation of 6-aminopenicillanic acid and 7-aminocephalosporanic acid and like nucleus compounds. For example, an active derivative of the carboxylic acid such as an acid halide, active ester, mixed anhydride, or acid azide can be used in the coupling reaction. For example, 1-[α-(benzyloxycarbonyl)benzyl]-3-methylthio-3β-aminoazetidin-2-one can be acylated with 2-thienylacetyl chloride in aqueous acetone in the presence of an acid-binding agent such as triethylamine or pyridine to provide 1-[α-(benzyloxycarbonyl)benzyl]-3-methylthio-3β-(2-thienylacetamido)azetidin-2-one. In a further example, 1-[α-(4-methoxybenzyloxycarbonyl)-4-methoxybenzyl]-3-methyl-3β-aminoazetidin-2-one is acylated with D-phenylglycyl chloride hydrochloride in the presence of a weak base such as pyridine to provide 1-[α-(4-methoxybenzyloxycarbonyl)-4-methoxybenzyl]-3-methyl-3β-phenylglycylamidoazetidin-2-one represented by the formula

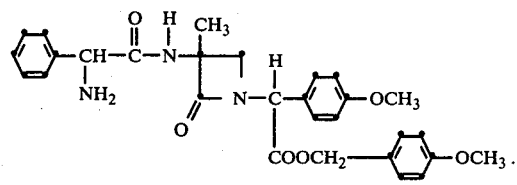

The 3-methoxy-4-acetoxyazetidin-2-ones (formula 1, $R_2$ = methoxy and $R_3$ = acetoxy) are also prepared by the methoxylation procedure described above with an N-acyl derivative of the 4-acetoxy nucleus (3). As an example, 1-[α-(benzyloxycarbonyl)-4-(3-chloro-4-methoxybenzyl)]-3β-amino-4α-acetoxyazetidin-2-one is acylated with 4-chlorophenylmercaptoacetyl chloride in the presence of triethylamine to provide the 3β-acylated ester of the formula

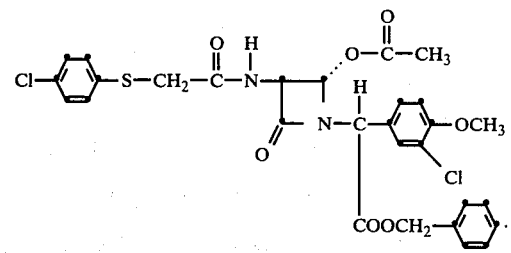

The above acylated product is then methoxylated with lithium methoxide/methyl alcohol/t-butylhypochlorite by the previously described procedure to provide the corresponding 3-methoxy ester. The benzyl ester group is removed via catalytic hydrogenolysis over palladium on carbon to provide the antibiotic compound of the invention represented by the formula

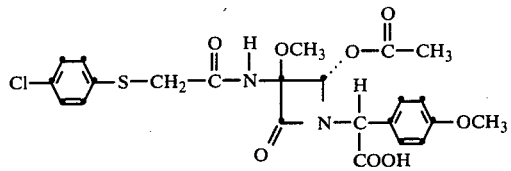

The 3β-aminoazetidin-2-ones represented by the above formulas (2) and (3) are prepared as now discussed below.

Preparation of 3β-aminoazetidin-2-ones and 3β-amino-4α-acetoxyazetidin-2-ones

As previously described herein the compounds of the formula (1) wherein R is an acylamino group are prepared with the 3β-aminoazetidin-2-ones represented by the formulas (2) and (3). The esterified 1-[α-(carboxy)-substituted benzyl]-3β-aminoazetidin-2-one represented by the formula (2) is prepared according to the method described in copending application Ser. No. 739,161 filed Nov. 5, 1976. According to this method L-cysteine is reacted with dry acetone at the reflux temperature to provide 2,2-dimethyl-4-thiazolidinecarboxylic acid. The product is acylated with benzoyl chloride in the presence of propylene oxide to provide 3-benzoyl-2,2-dimethyl-4-thiazolidinecarboxylic acid represented by the following formula.

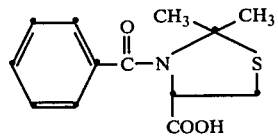

The thiazolidinecarboxylic acid is coupled with an ester of a phenylglycine represented by the formula,

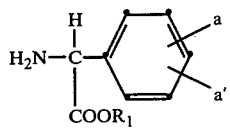

wherein a, a', and R₁ are as defined herein to form the amide represented by the following formula

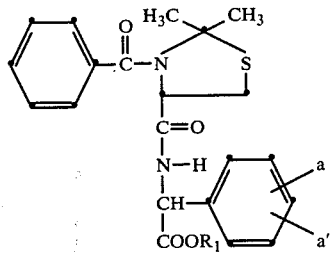

The coupling reaction is carried out by first preparing the active ester of the thiazolidinecarboxylic acid formed with 1-hydroxybenzotriazole (HBT) with dicyclohexylcarbodiimide and condensing the active ester and the phenylglycine ester.

Phenylglycine esters which can be used to form the above amides include for example, benzyl phenylglycinate, 4-methoxybenzyl phenylglycinate, benzyl 4-methoxyphenylglycinate, benzyl 4-chlorophenylglycinate, benzyl 3,4-dimethylphenylglycinate, benzyl 4-hydroxyphenylglycinate, 2,2,2-trichloroethyl phenylglycinate, 4-methoxybenzyl 3-chloro-4-hydroxyphenylglycinate, benzyl 4-t-butylphenylglycinate, benzyl 4-aminophenylglycinate, and 2,2,2-trichloroethyl 3,4-dichlorophenylglycinate. When the phenylglycine ester is substituted with a reactive functional group which can interfere with the desired coupling reaction (N-acylation), for example, a phenolic OH group or an amino group, such groups are blocked during the amidation reaction and in subsequent reactions in the process. The amino group can be blocked with the t-butyloxycarbonyl (t-BOC) group or the benzyloxycarbonyl group. A phenolic hydroxy substituent is best blocked with the benzyl group or tetrahydropyran group.

The thiazolidine amide of the above formula is then heated at the reflux temperature in a hydrocarbon solvent such as benzene or toluene with benzoyl peroxide to form the 5α-benzoate derivative represented by the formula

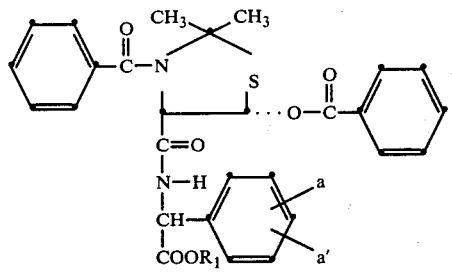

The benzoate is reacted in methylene chloride at about 0° C. with hydrogen chloride to form the corresponding 5α-chloro compound by replacement of the benzoate function. The 5α-chloro amide is reacted with sodium hydride under anhydrous conditions in a halogenated hydrocarbon solvent, such as methylene chloride, at a temperature between about 0° C. and about 30° C. to effect an intramolecular cyclization and provide the substituted thiazolidine azetidin-2-one represented by the following formula.

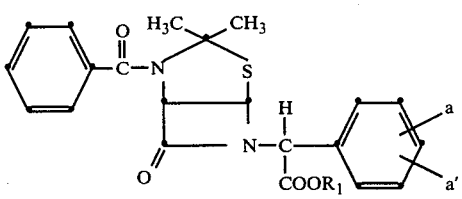

The thiazolidine azetidin-2-one is oxidized with a peracid such as m-chloroperbenzoic acid to provide the corresponding sulfoxide. The sulfoxide is treated in dimethylacetamide and benzene with methanesulfonic acid in the presence of water to provide, via an acid catalyzed rearrangement, the ring-opened 3-benzamido-azetidin-2-one represented by the formula

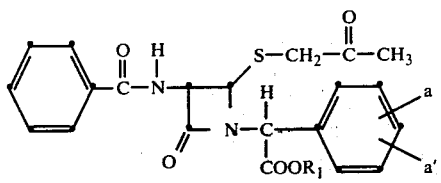

The 3-benzamido-azetidin-2-one is treated at a temperature of about 0° C. with sulfuryl chloride to form a reaction product mixture which via its nuclear magnetic resonance spectrum appears to comprise the 4-chloroazetidin-2-one and the oxazoline-azetidin-2-one represented by the following formulas.

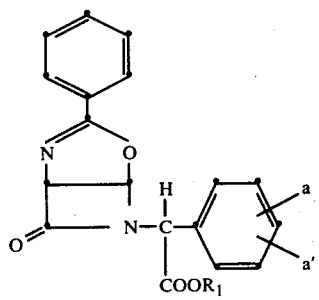

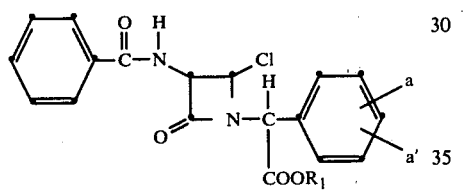

The reaction product mixture is reduced via a free radical reduction with tri-(n-butyl)tin hydride in the presence of azobisisobutyronitrile [2,2'-azobis-(2-methylpropionitrile)] to provide the 3-benzamidoazetidin-2-one represented by the following formula.

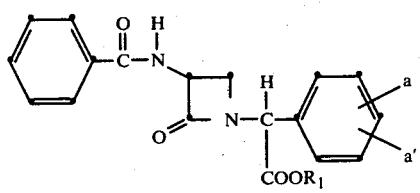

The 3β-aminoazetidin-2-one represented by the foregoing formula (2) is prepared with the above 3β-benzamidoazetidin-2-one ester by cleavage of the benzamido group. The cleavage is carried out by treating the benzamidoazetidin-2-one with phosphorus pentachloride in the presence of pyridine to form the intermediate benzimido chloride; reacting the benzimido chloride with methyl alcohol to form the benzimido methyl ether; and hydrolyzing the benzimido ether to the 3β-aminoazetidin-2-one ester.

As described previously herein the 3β-amino nucleus ester compounds (2) are converted to the 3β-amino-3-methyl and 3-methylthioazetidin-2-one esters [formula (1) wherein R is amino and $R_2$ is methyl or methylthio, and $R_3$ is hydrogen]. The latter on acylation provides compounds of the formula (1) wherein R is an acylamino group, $R_2$ is methyl or methylthio and $R_3$ is hydrogen.

The compounds of the formula (1) wherein $R_2$ is methoxy and $R_3$ is hydrogen are prepared as previously described herein with a 3β-acylaminoazetidin-2-one ester obtained via acylation of (2) followed by the described methoxylation.

The 3β-amino-4α-acetoxyazetidin-2-one ester represented by the following formula (3)

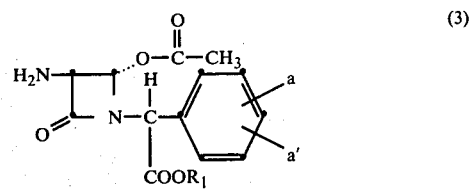

is used, as mentioned previously, in the preparation of the compounds of the invention represented by the formula (1) wherein R is amino or acylamino, $R_2$ is hydrogen, methyl, methylthio or methoxy, and $R_3$ is acetoxy. The 3β-aminoazetidin-2-one nucleus compound (3) is prepared by a novel process which is a further aspect of this invention.

According to the novel process a thiazolidine azetidin-2-one ester represented by the formula 4

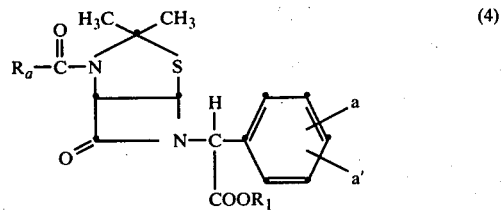

wherein $R_a$ is $C_1$–$C_3$ alkyl, phenyl, benzyl, or phenoxymethyl and $R_1$, a, and a' have the same meanings as previously defined herein; is reacted with mercuric acetate in acetic acid to form an ester of a 1-[α-(carboxy)benzyl or substituted benzyl]-3-(N-propenylacylamido)-4α-acetoxyazetidin-2-one represented by the following structural formula.

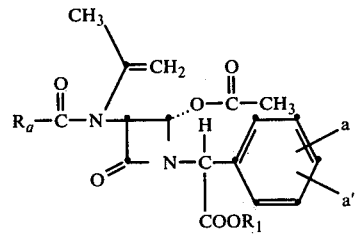

The N-propenylamide is converted to the 3β-acylamido-4α-acetoxyazetidin-2-one represented by the formula

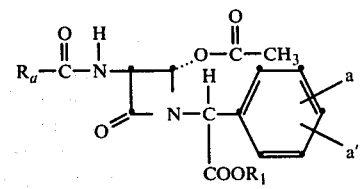

The removal of the N-propenyl group is carried out in a water-miscible solvent with a dilute mineral acid or with mercuric acetate in an aqueous solvent system. Aqueous solvent systems include water and a water miscible solvent, preferably aqueous tetrahydrofuran.

The hydrolysis product of the above formula is then N-deacylated via formation of the imido chloride with phosphorus pentachloride, conversion of the imido chloride to the corresponding imino ether with a lower alkanol such as methyl alcohol, and hydrolysis of the imido ether with water to provide the 3β-amino-4α-acetoxyazetidin-2-one of the formula (3).

The reaction of the thiazolidine azetidinone with mercuric acetate is carried out in acetic acid or in an inert co-solvent with acetic acid. Co-solvents such as tetrahydrofuran, dioxane, dimethylformamide, or dimethylacetamide can be used. A large excess of acetic acid is employed while between about 1 mole and about 3 moles of mercuric acetate per mole of the thiazolidine azetidinone is used. Preferably, about 1.5 to 2.0 moles of mercuric acetate per mole of starting material is employed.

The reaction is preferably carried out in acetic acid with heating at a temperature between about 25° and about 75° C. The reaction mixture is filtered after the reaction is complete to remove insoluble mercury compounds and the filtrate is evaporated. The product is then extracted from the residue with a water immiscible organic solvent such as ethyl acetate. The product, the N-propenylamide of the foregoing formula, need not be purified for its hydrolysis to the amide. The hydrolysis is best carried out between about 15° and about 55° C. in a water-miscible solvent, for example, tetrahydrofuran, with dilute hydrochloric acid, for example, between about 2 percent and 10 percent hydrochloric acid. Dilute sulfuric or dilute phosphoric acid can also be used. Alternatively, the hydrolysis is carried out in aqueous tetrahydrofuran, preferably 50% aqueous tetrahydrofuran, with mercuric acetate. Preferably an amount of mercuric acetate about equal in weight to the amount of N-propenylamine is employed. The hydrolysis can be carried out at a temperature between about 15° C. and about 45° C. and preferably at about 20° C. to about 25° C.

After the hydrolysis of the N-propenylamide is complete, the reaction mixture is evaporated and the residue containing the product is dissolved in a water immiscible solvent such as ethyl acetate and the solution is washed with a dilute base such as sodium bicarbonate to remove traces of acid. The product, an ester of 1-[α-(carboxy)benzyl or substituted benzyl]-3β-acylamido-4α-acetoxyazetidin-2-one represented by the foregoing formula is recovered from the washed solution and can be further purified by chromatography over silica gel.

The 3β-amino-4α-acetoxyazetidin-2-one is prepared as described above with the 3β-acylamido-4α-acetoxy hydrolysis product via N-deacylation with PCl₅/methanol/water.

In a preferred embodiment of the process 2-benzoyl-3,3-dimethyl-7-oxo-α-[4-(benzyloxy)phenyl]-4-thio-2,6-diazabicyclo[3.2.0]heptane-6-acetic acid, benzyl ester, informally named herein as benzoyl thiazolidine azetidinone, represented by the foregoing formula 4 wherein $R_a$ is phenyl, $R_1$ is benzyl, a is 4-benzyloxy and a' is hydrogen is reacted in acetic acid with mercuric acetate and the intermediate N-propenylbenzamide of the formula

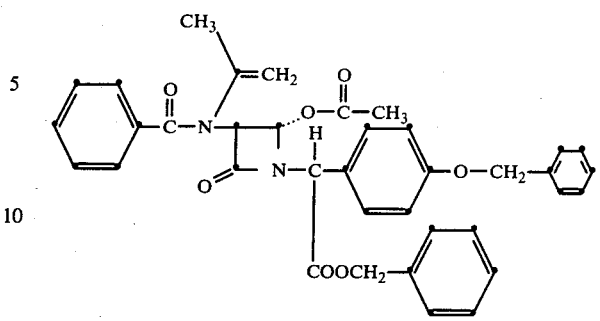

is hydrolyzed in tetrahydrofuran with 5 percent hydrochloric acid to provide 1-[α-(benzyloxycarbonyl)-4-benzyloxybenzyl]-3β-benzamido-4α-acetoxyazetidin-2-one represented by the formula.

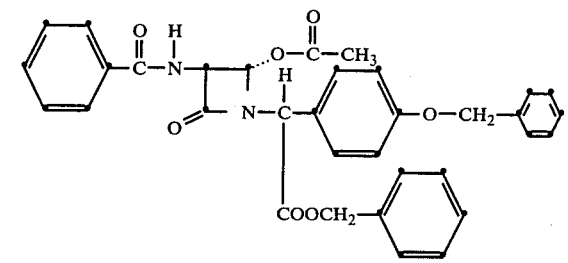

The 3β-benzamido ester is heated in dry benzene with excess phosphorus pentachloride in the presence of pyridine to form the benzimido chloride as illustrated in the partial structural formula.

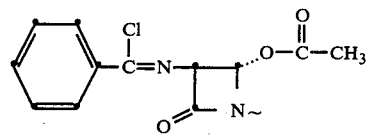

The reaction mixture is cooled to room temperature and excess dry methyl alcohol is added to form the corresponding methyl benzimido ether. The imido ether is hydrolyzed by the addition of aqueous tetrahydrofuran to yield 1-[α-(benzyloxycarbonyl)-4-benzyloxybenzyl]-3β-amino-4α-acetoxyazetidin-2-one represented by the foregoing formula (3) wherein $R_1$ is benzyl, a is 4-benzyloxy and a' is hydrogen.

In a further preferred embodiment of the process, 2-benzoyl-3,3-dimethyl-7-oxo-α-(4-hydroxyphenyl)-4-thia-2,6-diazabicyclo[3.2.0]heptane-6-acetic acid, diphenylmethyl ester, represented by the foregoing formula 4 when $R_a$ is phenyl, $R_1$ is diphenylmethyl, a is 4-hydroxy and a' is hydrogen, is reacted for about 10 minutes at steam bath temperatures in acetic acid with an equal weight of mercuric acetate to provide 1-[α-(diphenylmethoxycarbonyl)-4-hydroxybenzyl]-3-(N-propenylbenzamido)-4α-acetoxyazetidin-2-one represented by the formula,

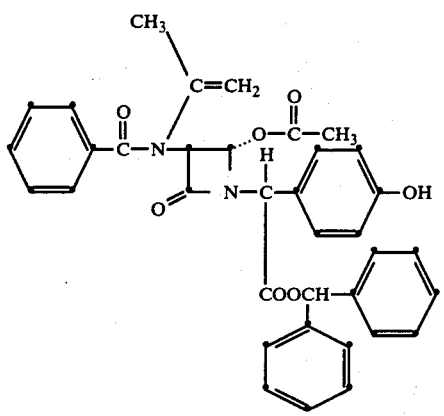

The intermediate N-propenyl ester is reacted at room temperature in tetrahydrofuran-water, 1:1 v:v, with an equal weight of mercuric acetate to provide the corresponding 3-benzamido ester. The 3-benzamido-4α-acetoxyazetidin-2-one ester is next reacted in tetrahydrofuran with dihydropyran in the presence of a catalytic amount of p-toluenesulfonic acid to provide the phenolic hydroxy-protected tetrahydropyranyloxy derivative of the formula.

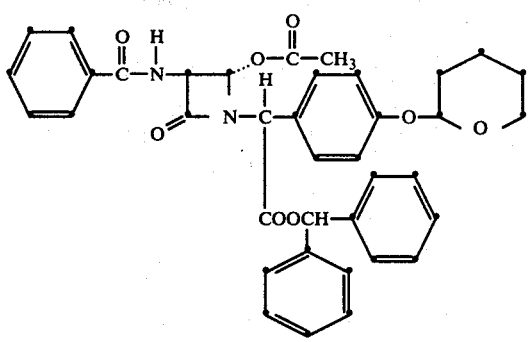

The above intermediate is then N-deacylated by treatment with phosphorus pentachloride in dry methylene chloride in the presence of pyridine followed by treatment with dry methanol and then with water to provide the 3β-amino-4α-acetoxyazetidin-2-one ester of the formula

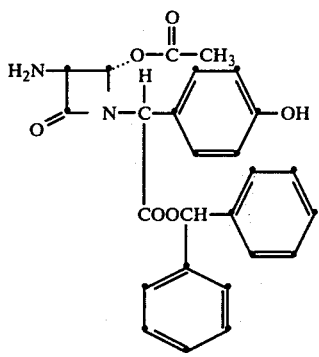

During the N-deacylation the tetrahydropyran group is also removed to provide the free phenolic hydroxy group as shown.

The above 3β-amino ester can be deesterified, if desired, to provide the corresponding carboxylic acid compound represented by the formula 3 when $R_1$ is hydrogen, a is 4-hydroxy and a' is hydrogen.

The thiazolidine azetidinone esters used as starting materials in the process are prepared as described previously herein in connection with the preparation of the 3β-amino nucleus (2).

The 3β-amino-4α-acetoxy nucleus (3) is acylated with an active derivative of a carboxylic acid

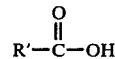

to provide the compounds of the invention where in formula (1) R is an acylamino group

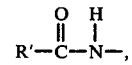

$R_2$ is hydrogen, and $R_3$ is acetoxy. The compounds of the invention represented by the formula (1) wherein $R_2$ is methyl or methylthio and $R_3$ is acetoxy are prepared with the 3β-amino-4α-acetoxy nucleus (3) by following the same synthesis routes used to prepared the compounds of formula (1) wherein $R_3$ is hydrogen and $R_2$ is methyl or methylthio. These synthetic procedures have been previously described herein. For example, the 3β-amino-4α-acetoxyazetidin-2-one of the formula (3) is condensed with p-nitrobenzaldehyde and the 3β-imine is alkylated with methyl iodide and sodium hydride. Removal of the p-nitrobenzal group with a carbonyl reagent, e.g., aminooxyacetic acid, affords the 3β-amino-3-methyl-4α-acetoxyazetidin-2-one represented by the formula (1) wherein R is amino, $R_2$ is methyl, and $R_3$ is acetoxy. Likewise, (3) is methylthiolated by reacting the p-nitrobenzylideneamino derivative of (3) with sodium hydride to generate the anion which is then reacted with methoxycarbonyl methyl disulfide to provide the 3β-(p-nitrobenzylideneamino)-3-methylthio-4α-acetoxyazetidin-2-one. Removal of the p-nitrobenzal group affords the compound of the formula 1 wherein R is amino, $R_2$ is methylthio, and $R_3$ is acetoxy.

The above synthetic routes are illustrated in the following reaction scheme.

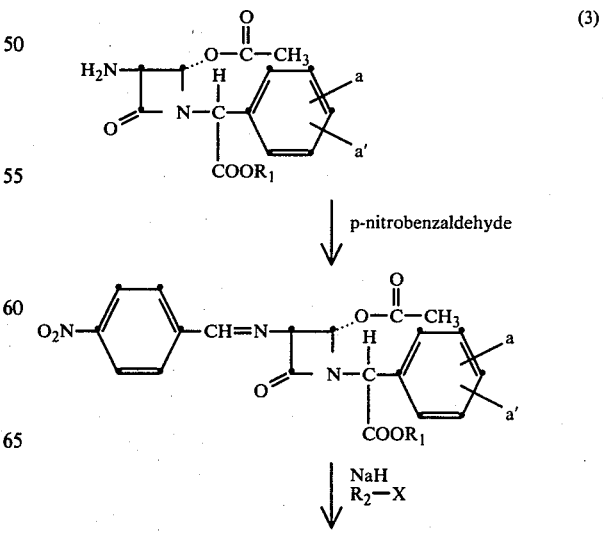

-continued

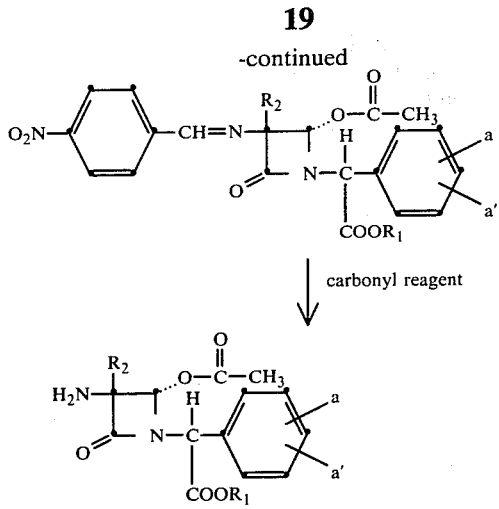

$R_2$ = CH$_3$ or CH$_3$—S
X = I when $R_2$ = CH$_3$, and

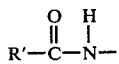

when $R_2$=CH$_3$—S.

The preparation of the compounds of the invention represented by the formula (1) wherein $R_2$ is methoxy and $R_3$ is acetoxy is carried out in the manner previously described herein for the methoxylation of compounds wherein $R_2$ is methoxy and $R_3$ is hydrogen which method employed nucleus (2). Accordingly, a 3β-amino-4α-acetoxyazetidin-2-one ester is acylated with an activated derivative of a carboxylic acid R'COOH to provide the compound of the formula (1) wherein R is and acylamino group

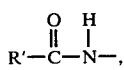

and $R_3$ is acetoxy. The 3β-acylamino compound is then reacted under anhydrous conditions at about −70° C. with lithium methoxide/t-butyl hypochlorite/methyl alcohol to provide the 3β-acylamino-3-methoxy-4α-acetoxyazetidin-2-one ester (formula 1, R =

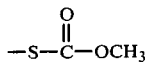, $R_2$ = CH$_3$O—, $R_3$ = oAc, and $R_1$ = ester).

In carrying out the methoxylation reaction, any hydroxy, amino, carboxy or other basic or acidic functions which are present in the molecule are blocked with a suitable protecting group. For example, in the formula (1) the acylamino group can be substituted in the α-position with amino, hydroxy, or carboxy groups as represented by the term Q. Likewise, the benzyl group in the 1-position of the azetidine ring can bear an amino or hydroxy substituent, as can a phenyl group of the 3-acylamino side chain when present. Such amino groups are blocked during the course of the methoxylation with a suitable amino-protecting group such as t-butyloxycarbonyl, benzyloxycarbonyl, 2,2,2-trichloroethoxycarbonyl, cyclopentyloxycarbonyl, and like groups. Such hydroxy substituent groups can be protected with benzyl, benzhydryl, 4-methoxybenzyl, 4-nitrobenzyl, 2,4,6-trimethylbenzyl, 3,5-dimethoxybenzyl, as well as with other suitable protecting groups. Such carboxy groups are best protected via formation of a carbon ester which is readily removed after the methoxylation under conditions which are non-destructive to the remainder of the molecule. Examples of carboxylic acid ester groups serving this function are benzyl, 4-nitrobenzyl, 4-methoxybenzyl, 3,5-dimethoxybenzyl, benzhydryl, 2,2,2-trichloroethyl, and other suitable groups forming carbon esters.

As described hereinbefore, the 3β-acylaminoazetidin-2-ones represented by the formula (1) wherein R is

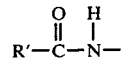

are prepared via the acylation of the 3β-amino nucleus compounds (2) and (3). The acylation is best carried out with an active derivative of the carboxylic acid R'—COOH. Active derivatives of these acids include the acyl halides such as the acid chlorides or bromides, the acid azides, and the mixed anhydrides formed with methyl chloroformate, ethyl chloroformate, or isobutyl chloroformate. Also, acylation can be carried out with the free carboxylic acid with a condensing agent such as dicyclohexylcarbodiimide as described in U.S. Pat. No. 3,218,318. The acylation of (2) and (3) is preferably carried out via the acid halide method or via the mixed anhydride method. The acylation via acyl halides can be carried out in an aqueous or non-aqueous solvent in the presence of a hydrogen halide acceptor such as sodium bicarbonate, a tertiary amine such as triethylamine or pyridine or an alkylene oxide such as propylene oxide or butylene oxide. The mixed anhydride method of acylation is carried out under anhydrous conditions in the presence of triethylamine.

The carboxylic acids

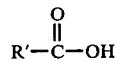

employed in the synthesis of the compounds of the formula (1) are readily available either from commercial sources or via known preparative methods.

The azetidin-2-one compounds represented by the formula (1) wherein

is an acyl group of the formula

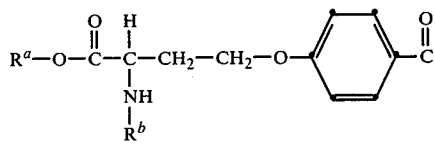

are prepared by acylating a 3β-aminoazetidin-2-one nucleus compound with the amino-protected and esterified 4-(3-carboxy-3-aminopropoxy)phenylglyoxylic acid, the oxime or protected oxime thereof. This acid and the oxime or protected oxime is prepared by the method described in co-pending application Ser. No. 739,160 filed on Nov. 5, 1976 and its continuing application Ser. No. 825,344 filed Aug. 17, 1977.

As described therein, an amino protected salt of D-methionine of the formula

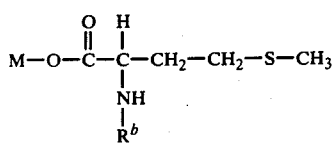

for example, the salt wherein M is dicyclohexylammonium and $R^b$ is as previously defined herein, is converted to the trimethylsilyl ester and is alkylated on the sulfur atom with an alkyl or benzyl iodide, for example, methyl iodide and the alkylsulfonium iodide of the formula

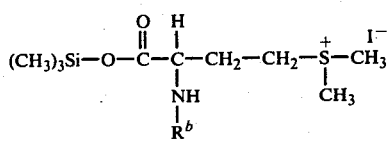

is reacted in an inert solvent with potassium t-butoxide to form the cyclic amino-protected D-homoserine lactone of the formula

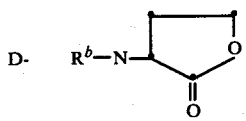

The lactone is hydrolyzed with an alkali metal hydroxide to the amino-protected D-homoserine alkali metal salt of the formula

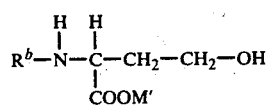

wherein M' is sodium or potassium, and the latter is converted to an acid labile ester e.g., diphenylmethyl ester. The esterified D-homoserine is then coupled with 4-hydroxyphenylglyoxylic acid p-nitrobenzyl ester with a trialkyl or triaryl phosphine and preferably triphenylphosphine and diethyl azodicarboxylate to form the amino-protected diester of the formula

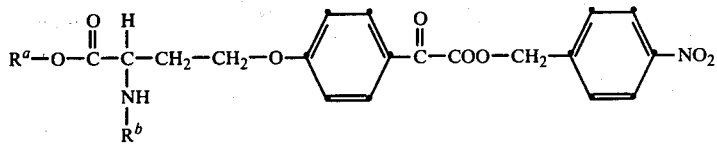

The p-nitrobenzyl ester group is selectively de-esterified by reduction whereby the other ester $R^a$, which is selected from among the acid-labile ester groups, remains substantially intact. For example, the p-nitrobenzyl ester group is removed via reduction with sodium sulfide while the ester group $R^a$, which can be an acid sensitive group such as the diphenylmethyl group, remains unaffected under the reduction conditions. The selective de-esterification product, the phenylglyoxylic acid, is represented by the formula

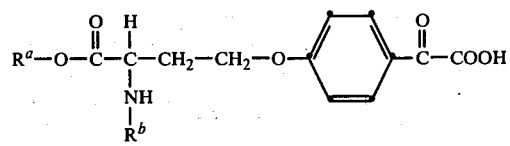

The amino-protected and esterified phenylglyoxylic acid is converted to an active ester which is used to acylate a 3β-aminoazetidin-2-one nucleus compound, for example (3). After acylation the α-ketoacylamide intermediate is converted to the biologically active oxime. For example, 4-[3-(t-butyloxycarbamido)-3-(diphenylmethoxycarbonyl)propoxy]phenylglyoxylic acid is converted to the active ester formed with 1-hydroxybenzotriazole by using dicyclohexylcarbodiimide as condensing agent and the ester is coupled with 1-[α-(benzyloxycarbonyl)-4-benzyloxybenzyl]-3β-amino-4α-acetoxyazetidin-2-one to provide 1-[α-(benzyloxycarbonyl)-4-benzyloxybenzyl]-3β-[4-(3-t-butyloxycarbamido)-3-(diphenylmethoxycarbonyl)propoxy]-phenylglyoxylamido-4α-acetoxyazetidin-2-one represented by the following formula.

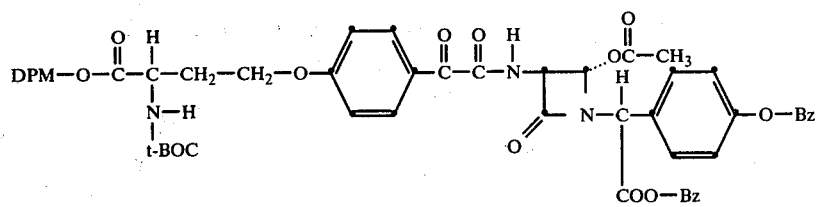

wherein DPM = diphenylmethyl; t-BOC = t-butyloxycarbonyl; and Bz = benzyl.

The above α-ketoamide is then converted to the oxime derivative with hyroxylamine hydrochloride in the presence of a weak base such as sodium bicarbonate, and the t-BOC group, the DPM and benzyl groups removed to provide the antibiotic of the formula (1) as shown below.

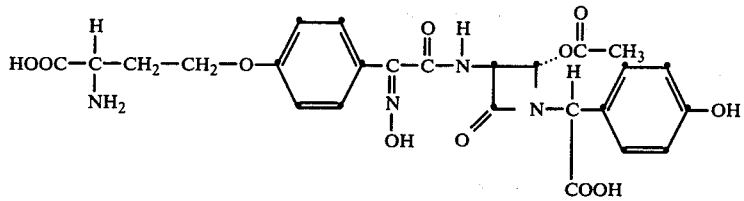

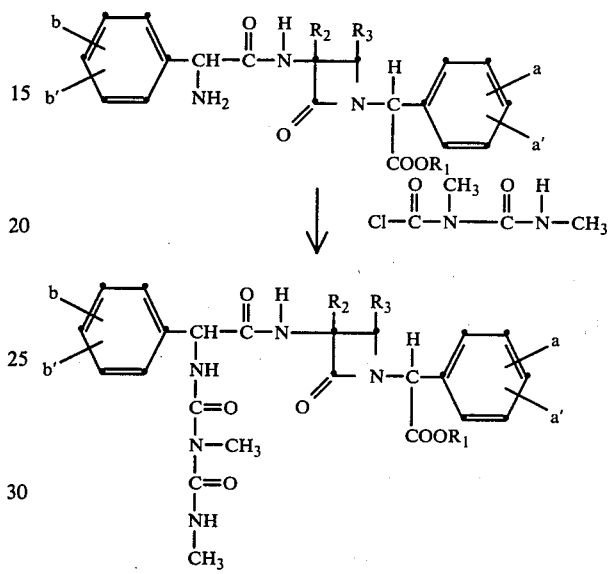

Alternatively, this nocardicin side chain can be synthesized by first forming the protected oxime of the 4-hydroxyphenylglyoxylic acid ester and then coupling the oxime ester with the amino-protected and esterfied D-homoserine fragment followed by selective de-esterification of the glyoxylic acid ester. For example p-nitrobenzyl 4-hydroxyphenylglyoxylate is reacted with hydroxylamine hydrochloride and the oxime is reacted with potassium t-butoxide followed by p-methoxybenzyl bromide to form the O-(p-methoxybenzyl)oxime. The oxime fragment is then coupled by the above described method with D-3-(t-butyloxycarbamido)-3-(diphenylmethoxycarbonyl)propanol (an amino protected and esterified D-homoserine) to form p-nitrobenzyl D-4-[3-(t-butyloxycarbamido)-3-(diphenylmethoxycarbonyl)propoxy]phenylglyoxylate O-(p-methoxybenzyl)oxime represented by the formula

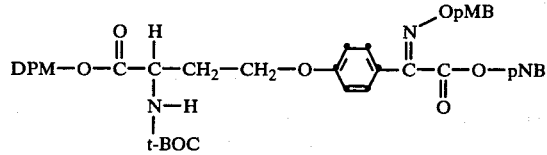

wherein DPM = diphenylmethyl, t-BOC = t-butyloxycarbonyl, pMB = p-methoxybenzyl and pNB = p-nitrobenzyl.

The p-nitrobenzyl ester group is then removed by chemical reduction for example with zinc and acid or by electrolytic reduction to provide the free carboxylic acid for acylation of the 3β-amino nucleus of the formula 2 or 3.

The compounds of the formula 1 wherein R' is a group of the formula

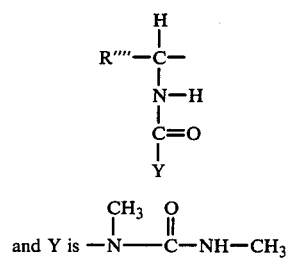

and Y is —N(CH$_3$)—C(O)—NH—CH$_3$ are prepared with a 3β-phenyl(thienyl or furyl)glycyclamidoazetidin-2-one by acylation of the α-amino group of the phenylglycylamido side chain with a carbamoyl chloride as shown below.

When Y in the formula 1 is the cyclic imidazolidine group or an acylureido group, the α-amino group is acylated with the N-chlorocarbonyl compounds

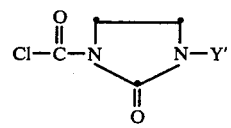

and

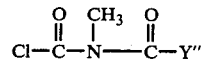

wherein Y' and Y" have the same meanings as defined above.

The dimethylureido, imidazolidin-2-one and acylureido carbonyl chlorides used in the acylation are prepared by reacting the 1,3-dimethylurea, imidazolidin-2-one or the N-methylamide with phosgene. For example, a cold (5° C.) suspension of sym-dimethylurea in dichloroethane is treated with a cold solution of phosgene in dichloroethane and after addition is complete, the mixture is stirred and allowed to warm to room temperature. Thereafter the reaction mixture is heated to about 80° C. to complete the reaction. Likewise, 2-imidazolidin-2-one-1-ylcarbonyl chloride is prepared in dry tetrahydrofuran with the imidazolidin-2-one and phosgene.

When Y in the formula 1 represents an N-methylacyl group

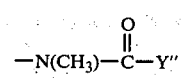

wherein Y" is $C_1$-$C_4$ alkyl, phenyl, or styryl, the corresponding N-methylamide is reacted with phosgene and the N-chlorocarbonyl-N-methylamide is used to acylate the α-amino group of the phenylglycyl side chain of the starting material. Examples of N-methylamides which are used to prepare the compounds of the formula 1 wherein Y is an N-methylacyl group are N-methylacetamide, N-methylbutyric acid amide, N-methylbenzamide, N-methyl-o-chlorobenzamide, N-methyl-p-nitrobenzamide, N-methylcinnamide, N-methyl-p-chlorocinnamide, and N-methyl-p-nitrocinnamide.

Examples of the above azetidin-2-ones are listed in the table below with reference to the following structural formula.

cleus compound represented by the formula (5) with an acid chloride of the oximino or methoximino acid

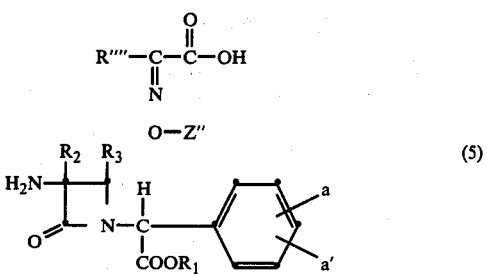

The acylation is carried out in an aqueous or non-aqueous solvent system, for example, in aqueous acetone or in ethyl acetate, methylene chloride, or tetrahydrofuran, in the presence of a hydrogen halide acceptor such as triethylamine or pyridine and in the instance where an aqueous solvent system is used an inorganic acid acceptor such as sodium bicarbonate can be used.

The α-oximino and α-methoximino phenyl, substituted phenyl, thienyl, or furylacetic acids are prepared in the known manner with the corresponding glyoxylic acids and hydroxylamine or methoxyamine. For example, phenylglyoxylic acid is reacted with methoxyamine

| R"" | Y | $R_2$ | $R_3$ | a | a' |
|---|---|---|---|---|---|
| phenyl | —N(CH$_3$)C(=O)—NH—CH$_3$ | H | oAc | H | H |
| phenyl | —N(CH$_3$)C(=O)—NH—CH$_3$ | H | oAc | 4-OH | H |
| phenyl | —N(CH$_3$)C(=O)—NH—CH$_3$ | OCH$_3$ | oAc | 4-OH | H |
| 2-thienyl | —N(CH$_3$)C(=O)—NH—CH$_3$ | H | oAc | H | H |
| 2-furyl | —N(CH$_3$)C(=O)—NH—CH$_3$ | H | oAc | H | 3-OH |
| 4-hydroxyphenyl | —N(CH$_3$)C(=O)—NH—CH$_3$ | —CH$_3$ | oAc | H | H |
| phenyl | 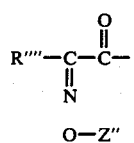 | H | oAc | 4-OH | 3-Cl |
| phenyl | (diazetidinone with N—SO$_2$CH$_3$) | —OCH$_3$ | oAc | H | H |
| 2-thienyl | —NHC(=O)—CH=CHφ | H | oAc | 4-OH | 3-CH$_3$ |
| 2-furyl | —NHC(=O)—CH$_3$ | OCH$_3$ | H | H | H |
| phenyl | —NH—C(=O)—φ | —SCH$_3$ | H | H | 3-NH$_2$ |

The compounds represented by the formula 1 wherein R is an acyl group of the formula $$R''''-C(=NOZ'')-C(=O)-$$

and R"" and Z" have the previously defined meanings are prepared by acylating a 3-aminoazetidin-2-one nuby the known procedure as described in British patent specification No. 1,399,086 published June 25, 1975. The oximino or methoximino acids are then converted to the said chloride with oxalyl chloride for acylation of the nucleus (5).

Alternatively, the oximino or methoximino acid can be converted to an active ester such as the pentachlorophenyl ester formed with pentachlorophenol and the active ester used to acylate the nucleus compound (5).

Examples of the α-oximino and α-methoximino acids which are used to prepare the compounds of the formula (1) are 2-methoximino-2-phenylacetic acid, 2-methoximino-2-(4-methoxyphenyl)acetic acid, 2-hydroximino-2-phenylacetic acid, 2-hydroximino-2-(4-hydroxyphenyl)acetic acid, 2-hydroximino-2-(3-chloro-4-hydroxyphenyl)acetic acid, 2-methoximino-2-(3-chloro-4-hydroxyphenyl)acetic acid, 2-methoximino-2-(2,6-dimethoxyphenyl)acetic acid, 2-methoximino-2-(4-nitrophenyl)acetic acid, 2-hydroximino-2-(4-methylphenyl)acetic acid, 2-hydroximino-2-(2-thienyl)acetic acid, 2-methoximino-2-(2-thienyl)acetic acid, 2-hydroximino-2-(2-furyl)acetic acid, and 2-methoximino-2-(2-furyl)acetic acid.

Examples of the antibiotic compounds which are prepared via the acylation with the above α-oximino and α-methoximino acids are illustrated in the following table.

$$R''''-\underset{\underset{O-Z''}{\overset{\|}{N}}}{\overset{O}{C}}-\overset{H}{\underset{|}{C}}-N\begin{array}{c}R_2\ R_3\\ \text{(azetidinone-phenyl ring)}\end{array}$$

| R'''' | Z'' | R₂ | OCH₃ | a | a' |
|---|---|---|---|---|---|
| phenyl | H | H | oAc¹ | H | H |
| phenyl | CH₃ | H | oAc | 4-OH | H |
| phenyl | CH₃ | OCH₃ | H | H | H |
| phenyl | H | H | oAc | 4-OH | H |
| phenyl | CH₃ | SCH₃ | H | H | H |
| phenyl | CH₃ | CH₃ | H | 4-OH | H |
| phenyl | CH₃ | CH₃ | oAc | H | H |
| phenyl | CH₃ | OCH₃ | oAc | 4-OH | H |
| phenyl | H | H | oAc | 4-OH | 3-Cl |
| phenyl | CH₃ | SCH₃ | oAc | 4-OH | H |
| 2-thienyl | CH₃ | H | oAc | H | H |
| 2-thienyl | H | H | oAc | 4-OH | H |
| 2-thienyl | CH₃ | OCH₃ | H | 4-Cl | H |
| 2-thienyl | CH₃ | SCH₃ | H | 4-CH₃ | H |
| 2-thienyl | CH₃ | SCH₃ | oAc | 4-nitro | H |
| 2-furyl | H | H | oAc | 4-OH | H |
| 2-furyl | CH₃ | H | oAc | 4-OH | H |
| 2-furyl | CH₃ | H | oAc | H | H |
| 2-furyl | CH₃ | OCH₃ | H | 4-OH | 3-Cl |
| 2-furyl | CH₃ | OCH₃ | oAc | H | H |
| 2-furyl | H | H | oAc | 4-Br | H |
| 2-furyl | CH₃ | SCH₃ | H | H | H |
| 2-furyl | CH₃ | SCH₃ | oAc | 3-CH₃ | 4-CH₃ |

¹acetoxy

The α-oximino and α-methoximino substituted azetidin-2-ones can have either the syn or anti configuration and their preparation as described above can lead to mixtures of both configurations. The preferred configuration is the syn configuration.

The isoxazol-4-yl acetamido and isoxazol-5-yl acetamido substituted azetidin-2-ones represented by the formula I wherein R'' is an isoxazol-4-yl or isoxazol-5-yl group are prepared by acylating the 3-amino nucleus compound (formula I, R = NH₂) with an active derivative of the carboxylic group of the appropriate isoxazolacetic acid. Active derivatives of the isoxazolacetic acids which can be used in the acylation of the nucleus compound include, for example, active ester for example, the 2,4-dinitrophenyl ester, the N-hydroxysuccinimide ester, the hydroxybenztriazol ester, and the ester formed with pentachlorophenol; the acyl halides thereof, for example, the acid chlorides and acid bromides; the active anhydrides formed with methyl chloroformate, ethyl chloroformate, or isobutyl chloroformate. Alternatively, the free acid may be used in the acylation by a coupling reaction employing a condensing agent such as a carbodiimide, for example, dicyclohexylcarbodiimide. These methods of acylation are commonly employed in the cephalosporin and penicillin art, for example, in the acylation of 6-aminopenicillanic acid or 7-aminocephalosporanic acid. To illustrate, the nucleus compound 1-[α-(benzyloxycarbonyl)-4-benzyloxybenzyl]-3β-amino-4α-acetoxyazetidin-2-one is acylated with 3-(2,6-dimethoxyphenyl)-5-methylisoxazol-4-ylacetyl chloride in methylene chloride or other suitable solvent in the presence of a hydrogen halide acceptor, for example, an alkylene oxide such as propylene oxide, or a tertiary amine such as triethylamine or an aromatic heterocyclic amine such as pyridine or quinoline to provide the acylation product, 1-[α-(benzyloxycarbonyl)-4-benzyloxybenzyl]-3β-[3-(2,6-dimethoxyphenyl)-5-methylisoxazol-4-ylacetamido]-4α-acetoxyazetidin-2-one.

The compounds of the formula I wherein R is an acylamino group of the formula, R''—CH₂C(O)—, and R'' is thienyl, furyl, thiazolyl, oxazolyl, isothiazolyl, or tetrazolyl are also prepared by acylating a 3-amino nucleus compound represented by the formula I (R=NH₂) with an active carboxylic acid derivative of the corresponding acetic acid R''—CH₂—COOH. Active derivatives of the acetic acids which can be employed in the acylation have been discussed previously hereinabove with respect to the preparation of other 3-acylamido azetidinones. Illustrative of the acetic acids are 3-thienyl acetic acid, 2-furyl acetic acid, thiazol-4-ylacetic acid, thiazol-5-ylacetic acid, oxazol-5-ylacetic acid and isothiazol-4-ylacetic acid. When in the formula I, R'' is phenyl or a substituted phenyl group, examples of phenyl and substituted phenylacetic acids which can be used in the acylation of the nucleus compound are for example phenylacetic acid, 2,6-dimethylphenylacetic acid, 4-chlorophenylacetic acid, 4-hydroxyphenylacetic acid, 4-isopropylphenylacetic acid, 3,4-dimethylphenylacetic acid, 3-hydroxyphenylacetic acid, 3-bromophenylacetic acid, 3-chloro-4-hydroxyphenylacetic acid, 4-aminophenylacetic acid, 2-aminoethylphenylacetic acid, and like mono and disubstituted phenylacetic acids.

Examples of the compounds of the invention represented by the formula I wherein R represents one of the foregoing R''—CH₂—C(O)—NH— groups are listed in the table below wherein reference is made to the following structural formula.

$$R''-CH_2-\underset{\underset{O}{\overset{\|}{N}}}{\overset{O}{C}}-\overset{H}{\underset{|}{N}}\begin{array}{c}R_2\ R_3\\ \text{(azetidinone-phenyl ring)}\end{array}$$

| R'' | R₂ | R₃ | a | a' |
|---|---|---|---|---|
| phenyl | H | oAc | H | H |
| 4-hydroxyphenyl | H | oAc | 4-OH | H |
| phenyl | OCH₃ | H | 4-OH | H |
| phenyl | SCH₃ | oAc | 3-OH | H |

-continued

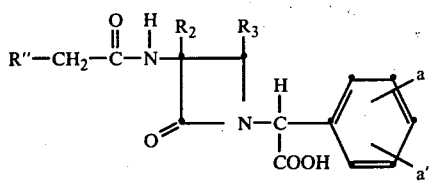

| R'' | R₂ | R₃ | a | a' |
|---|---|---|---|---|
| 2-thienyl | H | oAc | H | H |
| 2-thienyl | H | oAc | 4-OH | H |
| 2-thienyl | OCH₃ | H | 4-OH | 3-Cl |
| 2-furyl | H | oAc | H | H |
| 2-furyl | OCH₃ | oAc | 4-NH₂ | H |
| thiazol-4-yl | H | oAc | H | H |
| isothiazol-5-yl | H | oAc | 3-Br | H |
| oxazol-5-yl | OCH₃ | H | H | H |
| oxazol-5-yl | SCH₃ | H | 4-CH₃ | 3-CH₃ |
| oxazol-5-yl | H | oAc | 4-OH | H |
| 1H-tetrazol-1-yl | H | oAc | H | H |
| 1H-tetrazol-1-yl | OCH₃ | oAc | 4-NH—CH₂ | H |
| 1H-tetrazol-1-yl | SCH₃ | H | H | H |
| isoxazol-4-yl | H | oAc | H | H |
| 3-methyl-4-chloro-isoxazol-5-yl | H | oAc | 4-OH | H |
| 3-(2-chlorophenyl)-isoxazol-4-yl | OCH₃ | oAc | H | H |
| 3,4-dichloro-isoxazol-5-yl | H | oAc | 4-OH | 3-Cl |
| 3-chloro-4-methyl-isoxazol-5-yl | SCH₃ | H | H | H |
| 3,5-dimethylisoxazol-4-yl | H | oAc | 4-OCH₃ | 3-OCH₃ |

The compounds of the invention represented by the formula I wherein R is an acylamino group, R'''—S—CH₂— C(O)—NH—, R'''is phenyl, substituted phenyl, or 4-pyridyl are prepared by acylating the 3-aminoazetidine-2-one represented by the formula I (R = amino) with an active carboxylic acid derivative of phenylmercaptoacetic acid, a substituted phenylmercaptoacetic acid or 4-pyridylmercaptoacetic acid. The acylation can be carried out with an active derivative such as one of those mentioned hereinabove with respect to the preparation of other 3-acylamidoazetidin-2-ones.

The compounds of the formula I wherein R''' is thiazolyl, thiadiazolyl, or an oxadiazolyl group are prepared with a compound of the formula I wherein R represents the bromoacetamido or chloroacetamido group (R' = bromoethyl or chloromethyl) and a thiol of the appropriate heterocycle R'''—SH. The reaction is illustrated in the following general reaction scheme employing as an example the compound of the formula I wherein R is the bromoacetamido group and R''' is the 1,3,4-thiadiazol-2-thiol.

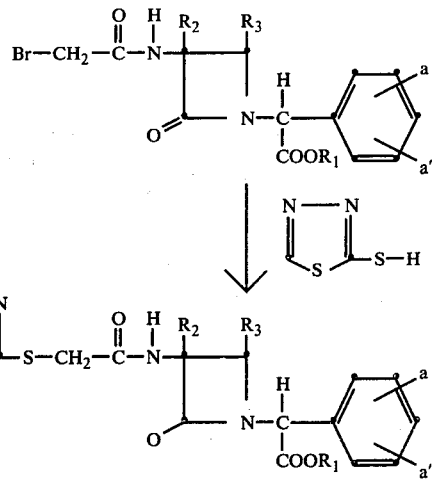

For example, 1-[α-(4-benzyloxycarbonyl)-4-methoxybenzyl]-3β-bromoacetamido-4α-acetoxyazetidin-2-one is dissolved in a polar organic solvent, for example, dimethylformamide or diemthylsulfoxide and a slight molar excess of 1,3,4-thiadiazol-2-thiol is added. The reaction can be carried out over a temperature range of between about 0° and 50° C.

Examples of the compounds of the invention wherein R is the acylamino group R'''—S—CH₂—C(O)— are given in the table below with reference to the following structural formula.

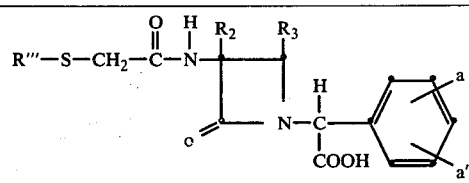

| R''' | R₂ | R₃ | a | a' |
|---|---|---|---|---|
| phenyl | H | oAc | H | H |
| phenyl | OCH₃ | oAc | 4-OH | H |
| phenyl | SCH₃ | H | H | H |
| phenyl | CH₃ | oAc | 4-Cl | H |
| 3,4-dichloro-phenyl | H | oAc | 4-OH | 3-OCH₃ |
| 3,5-dichloro-phenyl | H | oAc | 4-OH | 3-Cl |
| 3-methyl-4-hydroxyphenyl | OCH₃ | H | 4-OH | H |
| 4-pyridyl | H | oAc | H | H |
| 4-pyridyl | OCH₃ | H | H | 3-OH |
| 4-pyridyl | SCH₃ | oAc | 3-Cl | H |
| 4-pyridyl | CH₃ | H | 4-Br | H |
| 4-pyridyl | OCH₃ | oAc | 3-OC₂H₅ | 4-OH |
| 2-thiazolyl | H | oAc | 4-OH | H |
| 1,3,4-thiadiazol-2-yl | SCH₃ | H | H | H |
| 1,3,4-thiadiazolyl-2-yl | H | oAc | 4-OH | 3-Cl |
| 1,3,4-oxadiazol-2-yl | OCH₃ | H | H | H |
| 1,3,4-oxadiazol-2-yl | H | oAc | 3-CH₃ | 4-CH₃ |
| 1,3,4-oxadiazol-2-yl | CH₃ | oAc | H | H |

The compounds of the invention represented by the formula I wherein R is an acylamino group

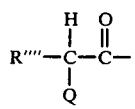

wherein R'''' is phenyl, substituted phenyl, thienyl, or furyl and Q is one of the above-defined substituent groups, are prepared by the acylation of a 3-aminoazetidin-2-one nucleus compound with the desired derivative of the substituted acetic acid represented by the following general formula.

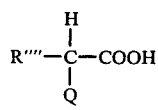

Examples of the above α-substituted acetic acids include the phenyl, thienyl, or furyl glycines when Q is amino; when Q is hydroxy, the mandelic and substituted mandelic acids, 2-(2-thienyl)-2-hydroxyacetic acid, and 2-(2-furyl)-2-hydroxyacetic acid; when Q is a carboxy group, the phenylmalonic acids and substituted phenylmalonic acids, 2-thienylmalonic acid, and 2-furylmalonic acid; the α-sulfo substituted acetic acids wherein R'''' is phenyl, substituted phenyl, 2-thienyl, or 2-furyl; and the α-substituted acetic acids wherein Q is a sulfamino group, —NH—SO₃H, and R'''' is as previously defined. In the acylation of the nucleus compound, an active derivative of the carboxylic acid such as the acid chloride, a mixed anhydride formed with the haloformate esters such as methyl chloroformate or isobutyl chloroformate or other suitable active derivative of the carboxylic acid is first prepared for the acylation. The reactive α-substituent such as the amino, hydroxy, or carboxy group is protected with a suitable blocking group during the acylation process. Numerous carboxy, hydroxy, and amino-protecting groups which are employed in the penicillin and cephalosporin art for the protection of such groups during the chemical reactions can be employed in the preparation of the compounds described herein. For example, the amino group can be protected with the t-butyloxycarbonyl group or the 2,2,2-trichloroethoxycarbonyl group; the hydroxy group can be protected with the benzyloxycarbonyl group or a substituted benzyloxycarbonyl group, for example, 4-nitrobenzyloxycarbonyl or the protecting group formed by reacting the hydroxy group with methyl vinyl ether; and the α-substituents which are acidic such as the carboxy, sulfo, or sulfamino group can be protected with a suitable carboxylic acid blocking group for example an ester such as benzyl, a substituted benzyl group, for example, 4-nitrobenzyl, 4-methoxybenzyl, or 2,4,6-trimethylbenzyl, the diphenylmethyl ester group, the trihaloethyl ester groups for example 2,2,2-trichloroethyl, or other suitable carboxylic acid blocking group. These blocking groups for the above-defined functional groups represented by Q are selected from those groups recognized as functional blocking groups which are readily cleaved following the acylation of the nucleus.

The acylation of the nucleus with an active derivative of the above-defined α-substituted acetic acid wherein the α-substituent is blocked is carried out by following the acylation procedures described hereinbefore with respect to the preparation of other 3β-acylaminoazetidin-2-ones of the invention.

Examples of the compounds represented by the formula I wherein R is an acyl group as previously defined are listed below with reference to the following structural formula.

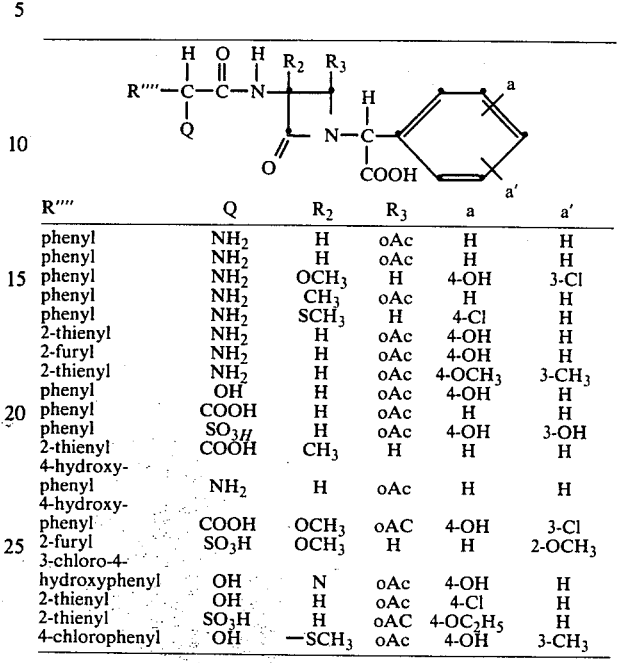

| R'''' | Q | R₂ | R₃ | a | a' |
|---|---|---|---|---|---|
| phenyl | NH₂ | H | oAc | H | H |
| phenyl | NH₂ | H | oAc | H | H |
| phenyl | NH₂ | OCH₃ | H | 4-OH | 3-Cl |
| phenyl | NH₂ | CH₃ | oAc | H | H |
| phenyl | NH₂ | SCH₃ | H | 4-Cl | H |
| 2-thienyl | NH₂ | H | oAc | 4-OH | H |
| 2-furyl | NH₂ | H | oAc | 4-OH | H |
| 2-thienyl | NH₂ | H | oAc | 4-OCH₃ | 3-CH₃ |
| phenyl | OH | H | oAc | 4-OH | H |
| phenyl | COOH | H | oAc | H | H |
| phenyl | SO₃H | H | oAc | 4-OH | 3-OH |
| 2-thienyl | COOH | CH₃ | H | H | H |
| 4-hydroxyphenyl | NH₂ | H | oAc | H | H |
| 4-hydroxyphenyl | COOH | OCH₃ | oAC | 4-OH | 3-Cl |
| 2-furyl | SO₃H | OCH₃ | H | H | 2-OCH₃ |
| 3-chloro-4-hydroxyphenyl | OH | N | oAc | 4-OH | H |
| 2-thienyl | OH | H | oAc | 4-Cl | H |
| 2-thienyl | SO₃H | H | oAC | 4-OC₂H₅ | H |
| 4-chlorophenyl | OH | —SCH₃ | oAc | 4-OH | 3-CH₃ |

The azetidin-2-ones represented by the formula 1 wherein R' is C₁-C₄ alkyl, cyanomethyl, bromomethyl, or chloromethyl are prepared by acylating the appropriate 3β-aminoazetidin-2-one nucleus with the C₁-C₄ alkanoic acid halide, cyanoacetyl halide, or bromo or chloroacetyl halide. Such halides include, for example, acetyl chloride, acetyl bromide, propionyl chloride, butyryl chloride, pivaloyl chloride, bromoacetyl chloride, chloroacetyl chloride, and cyanoacetyl chloride. The compounds represented when R' is phenyl are likewise prepared by the acylation of the appropriate nucleus with benzoyl chloride or benzoyl bromide. Alternatively, the benzoyl group of the 3β-benzamido substituted azetidin-2-one is present by virtue of being an acyl substituent of the intermediates used in the described synthesis of the nucleus compounds (2) and (3). For example, in the synthesis of the 3β-amino-4α-acetoxyazetidin-2-one the N-acyl group R_aC(O)— of the thiazolidine azetidinone described previously can be C₁-C₃ alkanoyl, phenylacetyl, benzoyl, or phenoxyacetyl and these groups remain intact during the process to provide the 3β-acylamino [(R_a—C(O)—] group of the 3β-acylamino-4α-acetoxyazetidinone product.

The 3β-acylaminoazetidin-2-ones represented by formula 1 wherein R₁, R^a, R^b and Z' are hydrogen and a and a' are other than benzyloxy or tetrahydropyran-2-yloxy, are useful antibiotics which inhibit the growth of pathogenic microorganisms. These compounds are resistant to inactivation by the β-lactamases and possess activity against the gram-negative bacteria which proliferate these enzymes, for example, proteus, pseudomonas, enterobacter sp., serratia and klebsiella.

The compounds are administered parenterally, for example, subcutaneously, intramuscularly or intravenously, preferably in the form of a pharmaceutically acceptable non-toxic salt.

The esterified, amino-protected, oxime-protected and hydroxy-protected azetidinones represented by the formula 1 are useful as intermediates in the synthesis of the antibiotic compounds.

The azetidin-2-one antibiotics represented by the formula 1 have an acidic carboxylic acid group which forms salts with suitable bases. Pharmaceutically acceptable salts include the alkali metal salts such as the sodium, potassium, or lithium salt; the calcium salt; salts formed with pharmaceutically acceptable amines, for example, mono- and diethanol amine, procaine, cyclohexylamine, dicyclohexylamine, dibenzylamine, abiethylamine, trimethylamine, or triethylamine.

3β-Acylaminoazetidin-2-ones of the formula 1 wherein Q is an amino group can form acid addition salts, for example, the hydrochloride or hydrobromide salts. Likewise, when the phenyl group substituent a or a' and b or b' is amino, acid addition salts of the antibiotics can be prepared.

Further, it will be appreciated that the 3β-amino and 3β-acylamino which contain an α-amino substituent in the side chain (Q = NH$_2$) can form intramolecular salts (zwitterions) when R$_1$ is hydrogen.

The 3β-aminoazetidin-2-one nucleus compounds represented by the formula 1 when R is an amino group are useful intermediates in the preparation of the 3β-acylaminoazetidin-2-one antibiotics. As described previously herein when the phenyl group of α-carboxybenzyl substituent in the 1-position of the azetidin-2-one ring is substituted with hydroxy or amino groups, such groups are preferably blocked with a suitable blocking group during synthesis for example, during N-acylation or N-deacylation. These nucleus compounds containing such blocked groups as well as esters of the nucleus compounds are also valuable intermediates. Examples of these nucleus compounds are listed below with reference to the following formula.

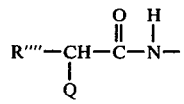

| R$_1$ | R$_2$ | R$_3$ | a | a' |
|---|---|---|---|---|
| H | H | oAc | H | H |
| H | H | oAc | 4-OH | H |
| benzyl | H | oAc | 4-benzyloxy | H |
| benzyl | CH$_3$ | H | 4-Cl | H |
| DPM[1] | OCH$_3$ | H | H | 2-Cl |
| pNB[2] | SCH$_3$ | H | 4-O—pNB | 3-Cl |
| pNB | H | oAc | 4-benzyloxy | 3-CH$_3$ |
| H | OCH$_3$ | oAc | 4-OH | H |
| H | SCH$_3$ | oAc | 4-OH | 3-Br |
| pMB[3] | H | oAc | 2-CH$_3$O | 4-CH$_3$O |
| H | H | oAc | 2-Cl | 6-Cl |
| pNB | H | oAc | 4-NH—BZ[4] | H |
| benzyl | H | oAc | 2-CH$_2$NHBz | H |

[1] diphenylmethyl
[2] p-nitrobenzyl
[3] p-methoxybenzyl
[4] benzyloxycarbonyl

The carboxylic acid protecting groups represented by R$_1$ in the formula 1 are carbon esters commonly used to temporarily protect or block the carboxylic acid function in other β-lactam antibiotics such as the penicillins and cephalosporins. Examples of these ester groups include the haloalkyl groups such as the trichloroethyl and tribromoethyl groups; the benzyl and substituted benzyl groups such as p-nitrobenzyl, p-methoxybenzyl, 3,5-dimethoxybenzyl, 2,4,6-trimethylbenzyl; diphenylmethyl (benzhydryl), 4-methoxydiphenylmethyl; or t-butyl. Methods for the removal of these ester groups are well known and are described in the literature.

As previously described herein, the 3-amino or 3-acylamino substituent R in the formula 1 has the β-configuration. The 4-acetoxy substituent group R$_3$ is provided in the α-configuration by the process described herein. During the synthesis of 3-methoxy, 3-methyl, or 3-methylthio-4-acetoxy substituted compounds as described herein, some epimerization of the 4α-acetoxy group may occur.

The α-carboxybenzyl or α-carboxy-substituted benzyl group substituted on the nitrogen atom of the azetidin-2-one ring (1-position) can have either the D or L configuration and the D configuration is preferred. The process for preparing 3β-amino-4α-acetoxyazetidin-2-one nucleus (3) described herein provides the preferred D-configuration when the phenylglycine employed in the process has the D-configuration.

Likewise the compounds of the formula 1 wherein R is the acylamino group $$R''''-CH-\overset{O}{\underset{|}{C}}-\overset{H}{\underset{|}{N}}-$$
$$\underset{Q}{|}$$

can have either the D or L configuration. The described compounds having the D configuration are preferred.

Certain of the compounds of this invention are preferred over others. For example, the compounds of the formula 1 wherein R$_3$ is acetoxy are preferred over those wherein R$_3$ is H. A preferred group is represented by the formula 1 when R is an acylamino group and R' is the acyl group of the formula

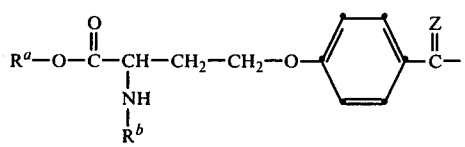

Preferred among these compounds are those wherein R$^a$ and R$^b$ are hydrogen, Z is the hydroxyimino group, a is 4-hydroxy, a' is hydrogen, and R$_3$ is α-acetoxy. An especially preferred compound is 4α-acetoxynocardicin represented by the formula

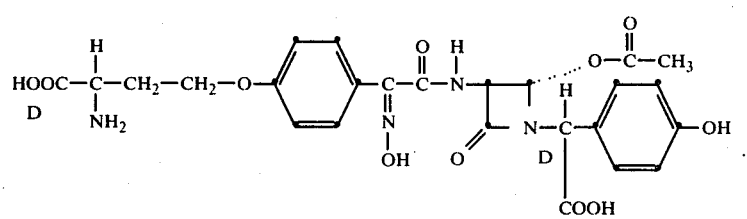

A preferred intermediate useful in the preparation of the above 4α-acetoxynocardicin is represented by the formula

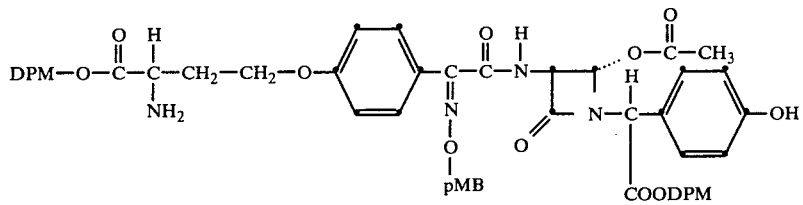

Another preferred group of compounds of this invention are represented when R is benzoylamino, phenylacetylamino, or phenoxyacetylamino, $R_2$ is hydrogen, and $R_3$ is acetoxy. These compounds are products of the process provided herein for the synthesis of the 4-acetoxy substituted azetidin-2-ones and can be used in the synthesis of the 3-amino-4-acetoxyazetidin-2-one nucleus (3) as previously described. They also can be methoxylated via the previously described methoxylation process, N-deacylated, and then reacylated with the desired carboxylic acid R'—COOH to afford the compounds of the formula 1 wherein $R_2$ is methoxy, and $R_3$ is acetoxy.

The following examples are provided to further describe the compounds and process of this invention.

EXAMPLE 1

Preparation of N-Benzoyl thiazolidine azetidinone benzyl ester

A slurry of 100 g. of L-cysteine in 2 l. of dry acetone was heated at the reflux temperature for about 17 hours. After the reaction mixture was allowed to cool to about 30° C. the unreacted cysteine was filtered and the reaction product, 2,2-dimethyl-4-thiazolidinecarboxylic acid, crystallized from the filtrate. Three crops of the product were obtained via successive filtrations. The combined weight of product was 83 g.

To a suspension of 16 g. (100 mM) of the product in 300 ml. of dry acetone were added 21 ml. of propylene oxide. Next, 11.6 ml. (100 mM) of benzoyl chloride were added dropwise with vigorous stirring. The temperature of the reaction mixture slowly increased from about 25° C. to about 33° C. After an hour all of the thiazolidine had dissolved and the reaction solution began to cool. When the temperature had dropped to 30° C. the reaction solution was evaporated to yield a white solid residue. The solid was dissolved in acetone and was diluted with hexane to crystallize the product. The product, 3-benzoyl-2,2-dimethyl-4-thiazolidinecarboxylic acid, was filtered and dried. The dried product weighed 18.7 g.

To a solution of 48 g. (181 mmole) of 3-benzoyl-2,2-dimethyl-4-thiazolidinecarboxylic acid, prepared by the procedure described above in 1.5 l. of tetrahydrofuran were added 27.8 g. (181 mmole) of 1-hydroxybenzotriazole followed by 37.4 g. (181 mmole) of dicyclohexylcarbodiimide. The mixture was stirred for 30 minutes at room temperature. The reaction mixture developed into a thick slurry resulting from the precipitation of dicyclohexylurea. To the heavy slurry was added 63 g. (181 mmole) of benzyl D-4-benzyloxyphenylglycinate and the reaction mixture was stirred at room temperature for about 2 hours. The reaction mixture was filtered to remove the dicyclohexylurea, the filtrate evaporated under reduced pressure, and the residue was dissolved in ethyl acetate. The solution was washed successively with 5% hydrochloric acid, water, aqueous sodium bicarbonate, and finally with water. The washed solution was dried, treated with carbon, and evaporated to dryness under reduced pressure to yield 107 g. (99% yield) of N-[α-(benzyl D-4-benzyloxyphenylacetate]-3-benzoyl-2,2-dimethyl-4-thiazolidinecarboxamide.

The above thiazolidinecarboxamide ester (107 g.; 0.18 mole) was dissolved in 4 l. of benzene and 175 g. (0.72 mole) of benzoyl-peroxide were added to the solution. The solution was then heated at the reflux temperature for 4.5 hours and thereafter was cooled to room temperature. The reaction mixture was poured over a column packed with silica gel and the column was eluted with benzene. Excess benzoyl peroxide passed off the column initially and on further elution with benzene, the product was collected. The eluate was evaporated under reduced pressure to provide the product, N-[α-(benzyl D-4-benzyloxyphenylacetate)]-3-benzoyl-2,2-dimethyl-4-thiazolidinecarboxamide-5α-benzoate, as an oil. The product was obtained crystalline from diethyl ether.

The above product is represented by the following structural formula

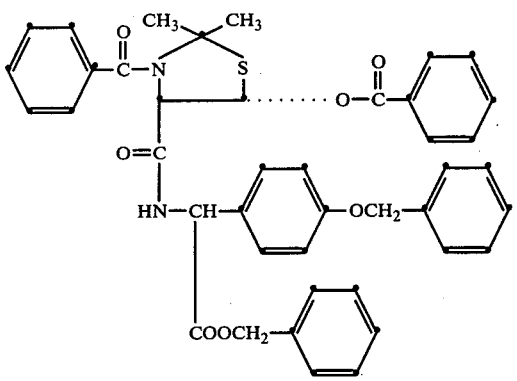

NMR (T60, CDCl$_3$): 2.16 (s, 2CH$_3$), 5.08 and 5.16 (2s, 2CH$_2$), 5.13 (s, CH), 5.54 (d, CH), 6.54 (s, CH) and 6.83–8.16 (m, aromatic H and NH) delta.

A solution of 25.5 g. (35.8 mmole) of the thiazolidine-4-carboxamide 5α-benzoate in 1 l. of dry methylene chloride was cooled to a temperature of 0° C. and hydrogen chloride was bubbled through the cold solution for about 2 hours. After this time, a thin layer chromatogram developed with benzene:ethyl acetate, 7:3, v:v, showed complete reaction. The methylene chloride was evaporated under reduced pressure providing the product as a foam. The foam was dissolved in ethyl acetate and the solution was washed with a dilute aqueous solution of sodium bicarbonate and with brine, and after washing was dried over magnesium sulfate, treated with carbon, and evaporated to dryness under reduced pressure. The product, N-[α-(benzyl D-4-benzyloxy-phenylacetate)]-3-benzoyl-2,2-dimethyl-5α-chloro-4-thiazolidinecarboxamide, represented by the following formula was obtained as 22.4 g. of white foam.

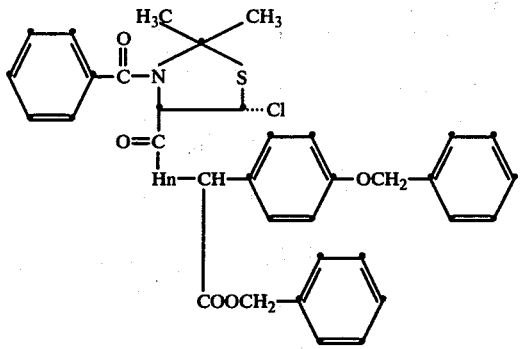

NMR (T60, CDCl₃): 2.12 (s, CH₃), 2.26 (s, CH₃), 5.08 and 5.16 (2s, 2CH₂) 5.16 (s, CH), 5.44 (d, CH), 5.83 (s, CH) and 6.08–7.5 (m, 2OH, aromatic H and NH) delta.

To a solution of 22.4 g. (35.8 mmole) of the 5α-chloro-4-thiazolidinecarboxamide in 800 ml. of methylene chloride and 200 ml. of dimethylformamide were added 1.72 g. of sodium hydride (50 percent in oil, 35.8 mmole). The reaction mixture was stirred at room temperature for approximately 50 minutes after which time TLC (benzene:ethyl acetate, 7:3) showed the reaction was complete. Two milliliters of acetic acid were added to the reaction mixture to destroy any excess sodium hydride, and the reaction mixture was poured into 5 percent hydrochloric acid. The organic phase was separated and was washed with 5 percent hydrochloric acid and with water before drying over magnesium sulfate. The dried extract was treated with carbon, filtered, and evaporated to dryness under reduced pressure. The residue was dissolved in about 30 ml. ethyl acetate. On standing, 10.1 g. (crop 1) of product crystallized. The crystals were filtered and the filtrate was treated with petroleum ether to the cloud point. On standing and with agitation, 5.5 g. (crop 2) of additional product crystallized. The second crop material was filtered and the filtrate was evaporated to dryness to yield further product as a foam. The foam was treated with a mixture of ethyl acetate and ethyl alcohol which afforded 2.2 g. of additional crystalline product (crop 3).

An analysis of the nuclear magnetic resonance spectrum (T-60) of the above crops demonstrated that crop 1 was the D isomer of the cyclized product represented by the formula shown below, crop 2 was the L isomer, while crop 3 was a mixture of the two isomers.

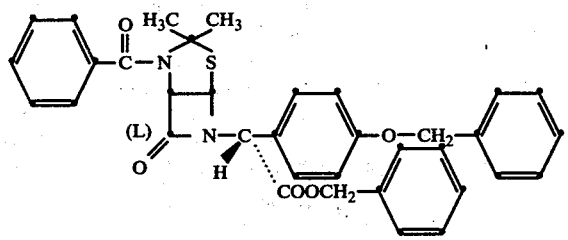

NMR (T60, CDCl₃): 1.70 (s, CH₃), 1.91 (s, CH₃), 5.08 and 5.16 (2s, 2CH₂), 5.45 (s, CH), 5.52 (m, 2CH), and 6.83–7.67 (m, 19H, aromatic H) delta.

The above thiazolidine azetidinone was also prepared with the 5α-chlorothiazolidine carboxamide and the base diazabicyclo[5.4.0]undec-5-ene(DBU) in the following manner.

A solution of 1.01 g. (1.6 mmole) of the 5α-chloro-4-thiazolidinecarboxamide having the D-configuration in 50 ml. of methylene chloride was cooled to a temperature of about 0° C. To the cold solution was added 0.243 g. (1.6 mmole) of DBU. The reaction mixture was stirred for 2 hours at 0° C. and then was washed with 5 percent hydrochloric acid and with brine and was then dried over magnesium sulfate. The solution was evaporated to yield a crude reaction product mixture. The mixture was crystallized from benzene/petroleum ether and the crystals filtered. The infrared spectrum of the product showed an absorption peak at 1775 cm⁻¹ for the β-lactam carbonyl, while the nuclear magnetic resonance spectrum and circular dichromism showed the material to be optically pure.

EXAMPLE 2

Preparation of 1-[α-benzyloxycarbonyl)-4-benzyloxybenzyl]-3β-benzamido-4α-acetoxyazetidin-2-one.

A slurry of 300 mg (0.505 mmole) of benzyl thiazolidine azetidinone in 25 ml. of acetic acid was stirred and treated with 240 mg. (0.75 mmole) of mercuric acetate. The reaction mixture was heated on the steam bath for 10 minutes, and an additional 100 mg. of mercuric acetate was added and heating was continued for 5 minutes. The reaction mixture was filtered to remove the insoluble mercurous acetate and was then evaporated to dryness. The residue was dissolved in ethyl acetate and the solution was washed with a dilute aqueous solution of sodium bicarbonate and with brine, was dried and then evaporated to dryness to yield 1-[α-(benzyloxycarbonyl)-4-benzyloxybenzyl]-3-(N-propenylbenzamido)-4-α-acetoxyazetidinone-2 represented by the following formula.

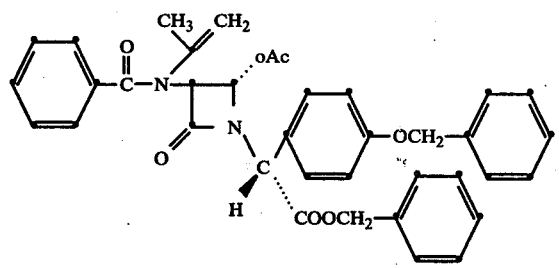

The product was dissolved in 50 ml. of tetrahydrofuran and 5 ml. of 5 percent hydrochloric acid were added. After stirring for 15 minutes at room temperature the solution was evaporated to dryness under reduced pressure and the residue was dissolved in ethyl acetate. The ethyl acetate solution was washed with a dilute aqueous solution of sodium bicarbonate, with water, and was dried and evaporated to dryness. The residue was chromatographed on a preparative silica gel thin layer plate using benzene:ethyl acetate, 7:3, v:v, for development to obtain 144 mg. of the hydrolysis product 1-[α-(benzyloxycarbonyl)-4-benzyloxybenzyl]-3-benzamido-4-α-acetoxyazetidinone-2.

EXAMPLE 3

By following the procedures described by Example 2 1-[α-(benzyloxycarbonyl)-4-benzyloxybenzyl]-3β- phenoxyacetamido-4α-acetoxyazetidin-2-one is prepared with the benzyl ester of the 3-phenoxyacetamido-thiazolidine azetidinone.

EXAMPLE 4

Preparation of 1-[α-(benzyloxycarbonyl)-4-benzyloxybenzyl]-3β-amino-4α-acetoxyazetidin-2-one To a solution of 250 mg. (0.432 mmole) of 1-[α-(benzyloxycarbonyl)-4-benzyloxybenzyl]-3-benzamido-4-α-acetoxyazetidinone-2 prepared as described in the foregoing example 2 in 50 ml. of dry benzene were added 132 mg. (0.64 mmole) of phosphorous pentachloride and 50 mg. (0.64 mmole) of pyridine. The mixture was heated to a temperature of about 65° C. for 2 hours with stirring. A thin layer chromatogram was then run on a reaction mixture and demonstrated the conversion of the starting material to the corresponding imido chloride.

The reaction mixture was evaporated under reduced pressure and 50 ml. of dry methyl alcohol were added to the residue. The methyl alcohol solution was stirred at room temperature for about 30 minutes. TLC of the solution showed a new spot.

The solution was evaporated under reduced pressure and 20 ml. of water and 20 ml. of tetrahydrofuran were added to the residue and the resultant solution was stirred at room temperature for about 20 minutes. The tetrahydrofuran was evaporated from the solution and the aqueous concentrate was slurried with ethyl acetate. The pH of the slurry was adjusted to pH 7 and the ethyl acetate layer was separated. The ethyl acetate layer was dried and then evaporated under reduced pressure to afford 210 mg. of a reduction product mixture. The nuclear magnetic resonance spectrum (T-60) of the product mixture showed it contained approximately 60 percent of the desired N-deacylation product, 1-[α-(benzyloxycarbonyl)-4-benzyloxybenzyl]-3-β-amino-4-α-acetoxyazetidinone-2 represented by the following structural formula.

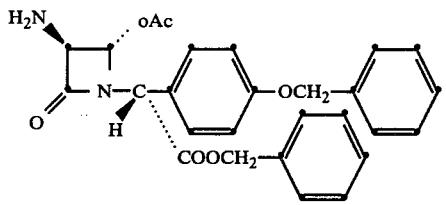

The crude product was purified via preparative thin layer chromatography on silica gel thick layer plates to yield 62 mg. of the product and 60 mg. of recovered starting material.

EXAMPLE 5

Preparation of 1-[α-(benzyloxycarbonyl)-4-benzyloxybenzyl]-3β-(p-nitrobenzylidene)amino-4α-acetoxyazetidin-2-one To a solution of 1-[α-(benzyloxycarbonyl)-4-benzyloxybenzyl]-3β-amino-4α-acetoxyazetidin-2-one in dry ethyl alcohol is added with stirring a slight molar excess of p-nitrobenzaldehyde. The solution is warmed on the steam bath for about 1 hour and the reaction mixture is concentrated under reduced pressure. The product is precipitated from the concentrate by adding petroleum ether, pentane, or cyclohexane.

EXAMPLE 6

Preparation of 1-[α-(carboxy)-4-hydroxybenzyl]-3β-(2-thienyl)acetamido-3-methylthio-4α-acetoxyazetidin-2-one The p-nitrobenzylidene derivative prepared as described by Example 5 is dissolved in anhydrous tetrahydrofuran and the solution is cooled under nitrogen with liquid nitrogen to a temperature of about −78° C. Lithium diisopropylamide is added to the cold solution with stirring followed by methoxycarbonyl methyl disulfide. The reaction mixture is stirred in the cold for 30 minutes, is acidified with acetic acid, is warmed to room temperature, and evaporated under reduced pressure. The product, 1-[α-(benzyloxycarbonyl)-4-benzyloxybenzyl]-3β-(p-nitrobenzylidene)amino-3-methylthio-4α-acetoxyazetidin-2-one, is extracted from the residue with ethyl acetate. The extract is washed, dried, and evaporated to dryness. The product is dissolved in tetrahydrofuran and an aqueous solution of aminooxyacetic acid hydrochloride is added to the solution. The mixture is stirred for 90 minutes and is concentrated to remove the tetrahydrofuran. The 3β-amino ester is extracted from the aqueous residue with ethyl acetate and after an acid-base wash the 1-[α-(benzyloxycarbonyl)-4-benzyloxybenzyl]-3β-amino-3-methylthio-4α-acetoxyazetidin-2-one is isolated.

The 3β-amino nucleus ester is dissolved in aqueous acetone and sodium bicarbonate is added. With stirring 2-thienylacetyl chloride is added. After stirring for 1 hour at 15° C. the acylation product is extracted from the mixture with ethyl acetate. The extract is washed, dried and evaporated to yield 1-[α-(benzyloxycarbonyl)-4-benzyloxybenzyl]-3β-(2-thienyl)acetamido-3-methylthio-4α-acetoxyazetidin-2-one.

The acylated ester is then reacted with hydrogen in the presence of 5 percent palladium on carbon to effect the de-esterification and debenzylation of the benzyl ester and provide the title compound.

EXAMPLE 7

Preparation of 1-[α-(carboxy)-4-hydroxybenzyl]-3β-(D-mandelamido)-4α-acetoxyazetidin-2-one To a solution of 1-[α-(p-nitrobenzyloxycarbonyl)-4-benzyloxybenzyl]-3β-amino-4α-acetoxyazetidin-2-one in tetrahydrofuran maintained at 0°–5° C. are added pyridine and O-formyl mandeloyl chloride. The mixture is stirred in the cold for about 2 hours and is then evaporated. Water is added to the residue and the acylation product is extracted with ethyl acetate. The extract is washed with water, dilute acid, and again with water and is dried and then evaporated to yield the esterified N-acylation product, 1-[α-(p-nitrobenzyloxycarbonyl)-4-benzyloxybenzyl]-3β-O-formylmandelamido-4α-acetoxyazetidin-2-one. The ester is de-esterified with zinc and hydrochloric acid during which the 4-benzyloxy group is removed to provide the title compound.

EXAMPLE 8

Preparation of 1-[α-(carboxy)-3-chloro-4-hydroxybenzyl]-3β-(2-thienyl)acetamido-3-methoxyazetidin-2-one A solution of 1-[α-(p-nitrobenzyloxycarbonyl)-3-chloro-4-benzyloxybenzyl]-3β-(2-thienyl)acetamidoazetidin-2-one in tetrahydrofuran is cooled to −78° C. in liquid nitrogen and excess methyl alcohol and methyl lithium are added followed by excess t-butyl hypochlorite. The reaction mixture is stirred in the cold for 45 minutes and is then acidified with acetic acid. The reaction mixture is warmed to room temperature, is diluted with water, and the product extracted with ethyl acetate. The extract is washed with water, brine, and a dilute solution of sodium carbonate and is dried and evaporated. The crude product is separated from unreacted starting material by chromatography over silica gel (15 percent water). The product is debenzylated and de-esterified with zinc and acetic acid to provide the title compound.

EXAMPLE 9

Preparation of
1-[α-(carboxy)-4-hydroxybenzyl]-3β-[2-[4-(3-carboxy-3-aminopropoxy)phenyl]-2-hydroximinoacetamido]-4α-acetoxyazetidin-2-one To a solution of 32 mg. of 1-[α-(benzyloxycarbonyl)-4-benzyloxybenzyl]-3β-amino-4α-acetoxyazetidin-2-one in about 5 ml. of dry methylene chloride were added 36 mg. of 4-(3-diphenylmethoxycarbonyl-3-t-butyloxycarbamidopropoxy)phenylglyoxylic acid. The mixture was stirred at room temperature under nitrogen and 14 mg. of dicyclohexylcarbodiimide were added. The solution immediately turned a dark yellow. After 10 minutes the solution became light yellow and dicyclohexylurea precipitated. A thin layer chromatogram of the mixture run on silica gel plates with benzene:ethyl acetate, 7:3, v:v, showed complete reaction. The reaction mixture was filtered and the filtrate was evaporated to dryness.

The acylation product was purified on preparative thick layer plates (silica gel) to yield 41 mg. of the purified intermediate product.

The product was reacted with hydroxylamine hydrochloride in aqueous tetrahydrofuran containing pyridine to form the hydroximino derivative. The oxime was reacted with trifluoroacetic acid in anisole to cleave both the t-BOC amino-protecting group and the diphenylmethyl ester group of the side chain. After treatment with the acid, the reaction mixture was evaporated to dryness and the residue was vigorously triturated with diethyl ether. The insoluble product, 1-[α-(benzyloxycarbonyl)-4-benzyloxybenzyl]-3β-[2-[4-(3-carboxy-3-aminopropoxy)phenyl]-2-hydroxyiminoacetamido]-4α-acetoxyazetidin-2-one trifluoroacetate salt, was filtered and dried.

The salt was dissolved in dry methylene chloride and was treated with a solution of excess aluminum chloride and anisole in nitromethane to effect the removal of both benzyl ester groups. The reaction mixture was quenched with water and the pH adjusted to about 8.0 with sodium bicarbonate. The solution was washed with ethyl acetate and was then chromatographed over Sephadex. The title compound was obtained as the disodium salt by evaporation of the eluate.

The course of the debenzylation reaction is followed by thin layer chromatography over silica gel using acetic acid:acetone, 4:1, v:v, for development.

EXAMPLE 10

Preparation of
1-[α-(diphenylmethoxycarbonyl)-4-hydroxybenzyl]-3β-amino-4α-acetoxyazetidin-2-one.

A solution of 4 g. of 2-benzoyl-3,3-dimethyl-7-oxo-α-(4-hydroxyphenyl)-4-thia-2,6-diazabycyclo[3.2.0]-heptane-6-acetic acid and 5 g. of diphenyldiazomethane in 500 ml. of dry tetrahydrofuran was stirred at room temperature for about 18 hours. The reaction mixture was evaporated under reduced pressure to dryness and the residue was dissolved in ethyl acetate. The diphenylmethyl ester product, 2-benzoyl-3,3-dimethyl-7-oxo-α-(4-hydroxyphenyl)-4-thia-2,6-diazabycyclo[3.2.0]heptane-6-acetic acid diphenylmethyl ester, crystallized from solution. 3.5 Grams of the diphenylmethyl ester were obtained.

To a suspension of 1 g. of the diphenylmethyl ester in approximately 100 ml. of acetic acid were added with stirring 1 g. of mercuric acetate. The reaction mixture was heated on the steam bath for approximately 10 minutes with continued stirring. The reaction mixture was filtered to remove the insolubles and was evaporated under reduced pressure to dryness. The reaction product mixture obtained as a residue was dissolved in ethyl acetate and the solution was washed with a dilute aqueous solution of sodium bicarbonate and with brine and was then dried and evaporated to dryness to yield 1.1 g. of 1-[α-(diphenylmethoxycarbonyl)-4-hydroxybenzyl]-3-(N-propenylbenzamido)-4α-acetoxyazetidinone-2.

The propenyl 4α-acetoxyazetidin-2-one diphenylmethyl ester, 650 mg. was dissolved in 50 ml. of water and 50 ml. of tetrahydrofuran and 650 mg. of mercuric acetate were added. The reaction mixture was stirred at about room temperature for approximately 1 hour. The reaction mixture was evaporated to dryness under reduced pressure and the residue containing the hydrolysis product was dissolved in ethyl acetate. The ethyl acetate solution was washed with a dilute aqueous solution of sodium bicarbonate, water, and was then dried and evaporated to dryness. The nuclear magnetic resonance spectrum (T60) showed that complete hydrolysis of the N-propenyl group had taken place. The product, 600 mg., 1-[α-(diphenylmethoxycarbonyl)-4-hydroxybenzyl]-3-benzamido-4α-acetoxyazetidinone-2 was used without further purification as described hereinafter.

To a solution of 510 mg. of the 4α-acetoxyazetidinone-2-diphenylmethyl ester prepared as described above in 40 ml. of dry tetrahydrofuran were added 2 ml. of dihydropyran and a small catalytic amount of p-toluenesulfonic acid. The reaction mixture was stirred at about room temperature for approximately 17 hours. A silica gel thin layer chromatogram showed the presence of starting material and the desired product, the tetrahydropyranyl ether formed with the 4-hydroxybenzyl group. With continued stirring approximately 0.5 g. of sodium carbonate were added to the reaction mixture. After stirring for 15 minutes the solvent tetrahydrofuran was evaporated and the residue was dissolved in ethyl acetate. The ethyl acetate solution was washed with sodium bicarbonate and with water and was then dried and evaporated to dryness. The starting material and product contained in the residue were separated on a silica gel chromatographic plate employing 7:3, toluene:ethyl acetate, v:v for elution. There were obtained 280 mg. of the product, 1-[α-(diphenylmethoxycarbonyl)-4-tetrahydropyranyloxybenzyl]-3-benzamido-4α-acetoxyazetidinone-2 and 178 mg. of recovered starting material.

To a solution of 78.5 mg. (0.38 mmole) of phosphorus pentachloride and 29.9 mg. (0.38 mmole) of pyridine in approximately 20 ml. of dry methylene chloride were added with stirring at room temperature under nitrogen 168 mg. (0.26 mmole) of the 4α-acetoxyazetidin-2-one tetrahydropyranyl ether diphenylmethyl ester. The reaction mixture was stirred at room temperature under nitrogen and periodically an aliquot was withdrawn from the reaction mixture and chromatographed on thin layer chromatography plates using benzene:ethyl acetate, 7:3 for elution. After approximately 1 hour the TLC showed only a trace of starting material and a new spot corresponding to the imino chloride. The methylene chloride was evaporated and 30 ml. of dry methyl alcohol were added to the concentrate. The methyl alcohol solution was stirred for approximately 2 hours at about room temperature. Thereafter, the methanol was evaporated and 20 ml. of water and 20 ml. of tetrahydrofuran were added to the residue. The aqueous solution was stirred for approximately 1 hour at about room temperature and thereafter the solution was evaporated to remove the tetrahydrofuran. The aqueous concentrate was extracted with ethyl acetate and the extract was dried and evaporated to dryness. The product obtained as a crude residue was purified via chromatography over silica gel to yield 81 mg. of 1-[α-(diphenylmethoxycarbonyl)-4-hydroxybenzyl]-3β-amino-4α-acetoxyazetidin-2-one.

EXAMPLE 11

Preparation of 4α-acetoxynocardicin

To a solution of 300 mg. (0.65 mmole) of the 4α-acetoxyazetidin-2-one nucleus diphenylmethyl ester prepared as described in the preceding example and 435 mg. (0.65 mmole) of 4-[3-(diphenylmethoxycarbonyl)-3-(t-butyloxycarbamido)propoxy]phenylglyoxylic acid O-(4-methoxybenzyl)oxime in approximately 25 ml. of dry methylene chloride maintained at about room temperature under nitrogen were added 135 mg. (0.65 mmole) of dicyclohexylcarbodiimide. The reaction mixture was stirred at approximately room temperature under nitrogen for about 2 hours. The reaction mixture was filtered and the filtrate was evaporated to dryness. The residue was chromatographed on a preparative silica gel chromatographic plate employing toluene::ethyl acetate, 1:1, v:v for elution to obtain 391 mg. of the acylated product, the t-butyloxycarbonyl protected amino, bis-dibenzhydryl ester protected and 4-methoxybenzyl protected oxime derivative of 4α-acetoxynocardicin represented by the formula below. The NMR of the product (T60) showed a trace impurity. The product was further purified in the same chromatographic system affording 332 mg. of the purified product.

yield 157 mg. of 4α-acetoxynocardicin trifluoroacetate salt.

NMR: DMSO($D_6$), $D_2O$ (Trimethylsilane reference, 1.95 (s, —C(O)$CH_3$), 2.31 (t, $CH_2$), 4.15 (t, and d, —CH—$CH_2$), 4.74 (d, —CH—), 5.20 (s, —CH—), 5.88 (d, —CH—) and 6.66–7.52 (aromatic H) delta.

We claim:
1. A compound of the formula

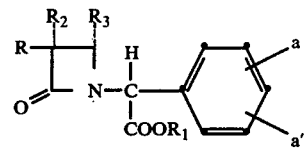

wherein a and a' independently are hydrogen, halogen, hydroxy, protected hydroxy, $C_1$-$C_4$ alkyl, $C_1$-$C_4$ alkoxy, amino, or protected amino, aminomethyl, or protected aminomethyl; R is amino or an acylamino group of the formula

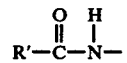

wherein R' is $C_1$-$C_4$ alkyl, cyanomethyl, bromomethyl, chloromethyl, phenyl, or a group of the formula

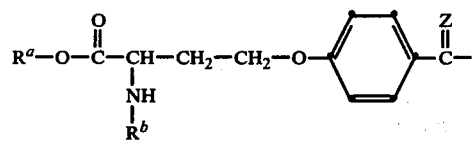

wherein
$R^a$ is hydrogen, benzyl, diphenylmethyl or 4-methoxybenzyl;
$R^b$ is hydrogen or an amino-protecting group of the formula

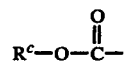

wherein $R^c$ is t-butyl, 2,2,2-trichloroethyl, benzyl, 4-nitrobenzyl, cyclopentyl, or cyclohexyl; Z is =O or =N—OZ', wherein
Z' is hydrogen, acetyl, chloroacetyl, triphenylmethyl or p-methoxybenzyl; or
R' is a group of the formula

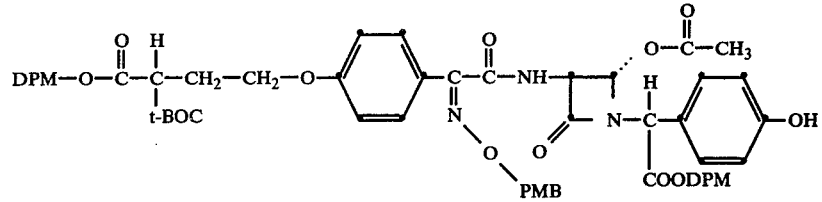

The protected bis-diphenylmethylester of 4α-acetoxynocardicin of the above formula was treated with 12 ml. of trifluoroacetic acid containing 24 drops of anisole at approximately room temperature for 3 minutes. The reaction mixture was evaporated to dryness and the residue was vigorously triturated with diethyl ether to

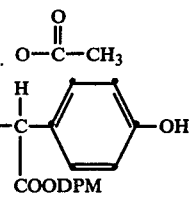

wherein R" is a phenyl group of the formula

wherein b and b' independently are hydrogen, halogen, hydroxy, $C_1$-$C_4$ alkyl, $C_1$-$C_4$ alkoxy, amino or aminomethyl; or
R" is thienyl, furyl, thiazolyl, oxazolyl, isothiazolyl, tetrazolyl, or an isoxazolyl group of the formula

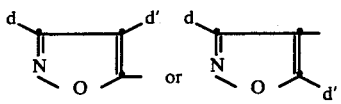

wherein d is hydrogen, methyl, or a group of the formula

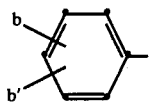

wherein b and b' have the same meanings defined above, and
d' is hydrogen, methyl, or chloro; or
R' is a phenoxymethyl group of the formula

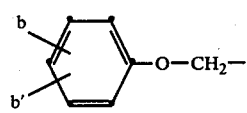

wherein b and b' have the same meanings as defined above; or
R' is a group of the formula

R'''—S—CH$_2$— wherein R''' is a group of the formula

4-pyridyl, thiazolyl, thiadiazolyl, or oxadiazolyl; or
R' is a group of the formula

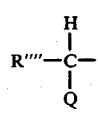

wherein R'''' is a phenyl group of the formula

thienyl or furyl, and Q is amino, hydroxy, carboxy, —SO$_3$H, or —NH—SO$_3$H; or
R' is a group of the formula

wherein R'''' has the same meanings as defined above and
Z" is hydrogen, acetyl or methyl; or
R' is a group of the formula

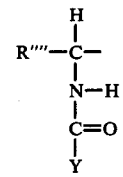

wherein R'''' is as defined above;
Y is a dimethylureido group of the formula

the imidazolidin-2-one group

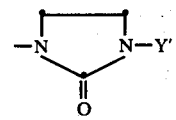

wherein Y' is hydrogen, $C_1$-$C_4$ alkyl, $C_2$-$C_4$ alkanoyl, or methanesulfonyl; or an N-methylacyl group of the formula

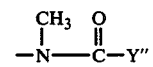

wherein Y" is $C_1$-$C_4$ alkyl, or a group of the formula

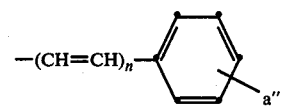

wherein n = 0 or 1 and a" is hydrogen, nitro, or chloro;
$R_1$ is hydrogen or a carboxylic acid protecting group;
$R_2$ is hydrogen, methyl, methylthio, or methoxy;
$R_3$ is hydrogen or acetoxy, provided that one of $R_2$ and $R_3$ is other than hydrogen; and when $R_1$ is hydrogen the pharmaceutically acceptable non-toxic salts thereof.

2. The compound of claim 1 wherein R is an acylamino group of the formula

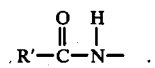

3. The compound of claim 2 wherein $R_2$ is methoxy and $R_3$ is hydrogen.

4. The compound of claim 3 wherein R' is a group of the formula

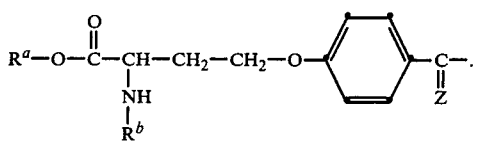

5. The compound of claim 3 wherein R' is a group of the formula

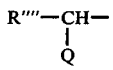

and Q is amino, hydroxy, or carboxy.

6. The compound of claim 3 wherein R' is phenyl, benzyl, or phenoxymethyl.

7. The compound of claim 3 wherein R' is phenyl.

8. The compound of claim 2 wherein $R_2$ is thiomethyl and $R_3$ is hydrogen.

9. The compound of claim 2 wherein $R_2$ is hydrogen and $R_3$ is acetoxy.

10. The compound of claim 9 wherein R' is a group of the formula

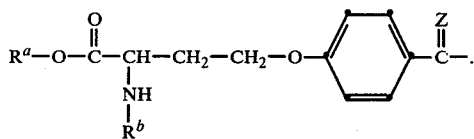

11. The compound of claim 10 wherein Z is =O.

12. The compound of claim 11 wherein Z is =N—OZ'.

13. The compound of claim 12 wherein $R^a$ is diphenylmethyl, $R^b$ is t-butyloxycarbonyl, $R_1$ is benzyl, a is 4-benzyloxy, a' is hydrogen and Z' is hydrogen.

14. The compound of claim 12 wherein $R^a$ and $R_1$ are diphenylmethyl, $R^b$ is t-butyloxycarbonyl, a and a' are both hydrogen and Z' is p-methoxybenzyl.

15. The compound of claim 12 of the formula

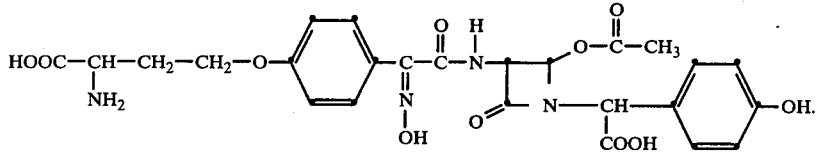

16. The compound of claim 9 wherein R' is a group of the formula

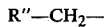

17. The compound of claim 16 wherein R" is phenyl, 2-thienyl, 2-furyl, or 1-tetrazolyl.

18. The compound of claim 9 wherein R' is a group of the formula

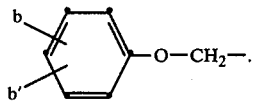

19. The compound of claim 9 wherein R' is a group of the formula

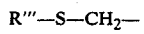

20. The compound of claim 9 wherein R' is a group of the formula

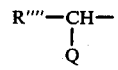

and Q is amino, hydroxy, or carboxy.

21. The compound of claim 9 wherein R' is a group of the formula

and R'''' is phenyl, 2-furyl, or 2-thienyl.

22. The compound of claim 9 wherein R' is a group of the formula

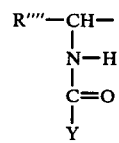

23. The compound of claim 22 wherein Y is a dimethylureido group of the formula

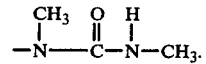

24. The compound of claim 22 wherein Y is a group of the formula

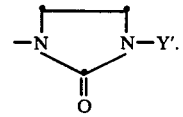

25. The compound of claim 22 wherein Y is an N-methylacyl group of the formula

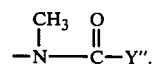

26. The compound of claim 9 wherein R' is phenyl, benzyl, or phenoxymethyl.

27. The compound of claim 1 wherein R is amino.

28. The compound of claim 27 wherein $R_2$ is hydrogen and $R_3$ is acetoxy.
29. The compound of claim 28 of the formula
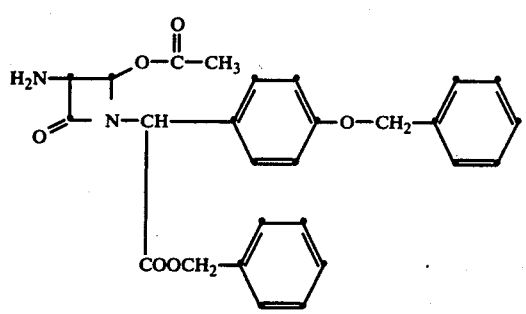
30. The compound of claim 28 of the formula
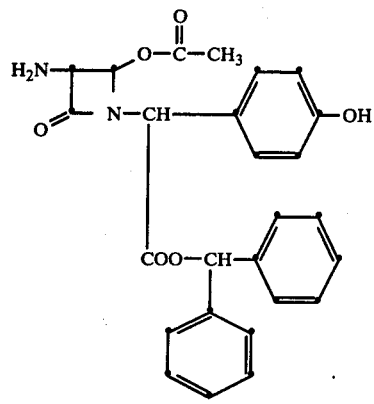
31. The compound of claim 28 of the formula
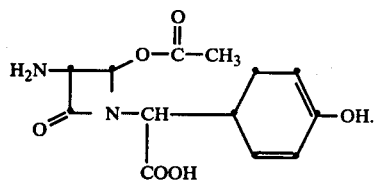
32. The compound of claim 27 wherein $R_2$ is methoxy, thiomethyl, or methyl.
* * * * *